United States Patent
Godden et al.

(10) Patent No.: US 10,953,220 B2
(45) Date of Patent: Mar. 23, 2021

(54) DEVICE AND METHOD OF SKIN CARE AND TREATMENT VIA MICRONEEDLES HAVING INHERENT ANODE AND CATHODE PROPERTIES, WITH OR WITHOUT COSMETIC OR PHARMACOLOGICAL COMPOSITIONS

(71) Applicant: CATURA CORPORATION, Seattle, WA (US)

(72) Inventors: Glenn Godden, Edmonds, WA (US); Darrick Carter, Seattle, WA (US)

(73) Assignee: CATURA CORPORATION, Seattle, WA (US)

( * ) Notice: Subject to any disclaimer, the term of this patent is extended or adjusted under 35 U.S.C. 154(b) by 71 days.

(21) Appl. No.: 16/423,850

(22) Filed: May 28, 2019

(65) Prior Publication Data

US 2019/0366072 A1 Dec. 5, 2019

Related U.S. Application Data

(63) Continuation of application No. 15/220,011, filed on Jul. 26, 2016, now abandoned.

(Continued)

(51) Int. Cl.
| | | |
|---|---|---|
| *A61N 1/04* | (2006.01) | |
| *A61N 1/32* | (2006.01) | |
| *A61M 37/00* | (2006.01) | |

(52) U.S. Cl.
CPC .......... *A61N 1/0416* (2013.01); *A61N 1/327* (2013.01); *A61M 2037/0007* (2013.01); *A61M 2037/0023* (2013.01); *A61M 2037/0061* (2013.01)

(58) Field of Classification Search
CPC ................. A61N 1/0416; A61N 1/327; A61M 2037/0007; A61M 2037/0023; A61M 2037/0061
See application file for complete search history.

(56) References Cited

U.S. PATENT DOCUMENTS

| | | | | |
|---|---|---|---|---|
| 2003/0069548 A1* | 4/2003 | Connelly | .......... | A61M 37/0015 604/264 |
| 2004/0078219 A1* | 4/2004 | Kaylor | ................... | G06Q 50/22 705/2 |

(Continued)

*Primary Examiner* — Lauren P Farrar
(74) *Attorney, Agent, or Firm* — Cozen O'Connor

(57) ABSTRACT

A device with in situ anode and cathode microneedles is used, either with or without any cosmetic, cosmeceutical, nutraceutical, and/or pharmaceutical composition or formulation. The in situ anode and cathode microneedles form battery cells or half-cells when placed in contact with an electrolyte found in bodily interface tissue, to produce an electromotive force without any additional chemical battery or power source. The microneedles may be composed of, or may carry (e.g., be coated with) electrical potential material(s) that has or have an electrical potential relative to an electrolyte in the bodily interface material. A first number of microneedles may, for instance, include a first electrical potential material having a first electrical potential. A second number of microneedles may, for instance, include a second electrical potential material having a second electrical potential. The first number of microneedles may thus serve as an anode, while the second number of microneedles may thus serve as a cathode. Alternatively, a number of microneedles may, for instance, include both a first electrical potential material and a second electrical potential material, having a first electrical potential and a second electrical potential, respectively. Respective portions of each of the microneedles may thus serve as an anode and a cathode. Again, such may be accomplished without any other or additional electrochemical battery.

13 Claims, 13 Drawing Sheets

Related U.S. Application Data

(60) Provisional application No. 62/288,305, filed on Jan. 28, 2016, provisional application No. 62/197,421, filed on Jul. 27, 2015.

(56) References Cited

U.S. PATENT DOCUMENTS

| | | |
|---|---|---|
| 2007/0083186 A1 | 4/2007 | Carter et al. |
| 2011/0276003 A1 | 11/2011 | Lüttge et al. |
| 2014/0142492 A1* | 5/2014 | Jung ................ A61M 37/0015 604/21 |
| 2014/0276362 A1* | 9/2014 | Alvarez ................ A61K 33/00 604/21 |
| 2015/0272906 A1* | 10/2015 | Jordan ................ A61M 35/00 604/20 |
| 2016/0213908 A1 | 7/2016 | McAllister et al. |

* cited by examiner

| PRODUCT | MULTI-OUTLET* | DRUG |
|---|---|---|
| ACNE TREATMENTS | 639 | 186.5 |
| BODY ANTI-AGING | 24.1 | 8.1 |
| DEPILATORIES | 191.2 | 70.5 |
| FACIAL ANTI AGING | 1,221.9 | 486.6 |
| FACIAL CLEANSERS | 963.4 | 294.6 |
| FACIAL MOSTURIZERS | 403.1 | 141.5 |
| FADE/BLEACH | 79.9 | 32.7 |
| TOTAL | 3,522.7 | 1,220.4 |

FIG. 1

DEVICE AND METHOD OF SKIN CARE AND TREATMENT VIA MICRONEEDLES HAVING INHERENT ANODE AND CATHODE PROPERTIES, WITH OR WITHOUT COSMETIC OR PHARMACOLOGICAL COMPOSITIONS

BACKGROUND

Technical Field

This disclosure generally relates to devices and methods that treat a biological interface tissue—for instance, skin. More particularly, this disclosure relates to devices and methods that treat biological interface tissue and which combine electric fields with cosmetic, cosmeceutical, nutraceutical, and pharmaceutical compositions to provide convenience, cosmetic, health, or medical benefits to an individual.

Description of the Related Art

Consumers spend billions of dollars per year on cosmetics and other skin care products. For example, Revlon, Inc.; Avon Products, Inc.; and L'Oréal reported combined sales of more than 30 billion dollars in recent years. Thus, at great expense, the majority of consumers passively apply cosmetics and skin care products on a daily basis. In part, the need to apply cosmetic and skin care products on a daily basis stems from the fact that many of today's cosmetic and skin care product formulations fail to significantly penetrate the outer layers of the skin when passively applied and when they do the "active ingredients" have questionable effects. This is especially problematic with regard to the application of "anti-aging" or "anti-wrinkle" skin care products.

In addition to cosmetics and other skin care products, many consumers require the application of medical treatments to prevent or treat a variety of frequently encountered skin disorders. For example, acne, psoriasis, eczema, dermatitis, xerosis, and ichthyosis often require the daily application of medical treatments to treat or ameliorate the conditions as well as the discomfort associated with the conditions. The discomfort associated with skin disorders includes, but is not limited to pain and itching.

Moreover, daily application of cosmetics, skin care products, and medical treatments is often very time consuming and expensive. Additionally, some medical treatments require costly and specialized devices or equipment that must be used at a doctor's office or treatment center under the supervision of a trained physician. These conditions lead to problems with patient compliance, which in turn, results in poor skin health and the increased chance of developing unwanted skin conditions.

Therefore, there is a need in the art for a more effective method for the application of cosmetics, skin health products, or medical treatments to the skin. The present disclosure provides devices, methods, and compositions to address these needs.

BRIEF SUMMARY

A device in the form of one or more of a nanoscale battery or batteries is safe and biocompatible and comprises a pharmaceutically accepted excipient base that is administered to a biological interface tissue (e.g., skin) of a user providing an organoleptic feedback as well as benefits from microcurrents elicited by the batteries. The device may be used by itself, or may be used to apply a cosmetic, cosmeceutical, nutraceutical, and/or pharmaceutical composition or formulation via one or more microneedles, that improves the user's experience and appearance results.

The device may be provided in the form of a patch. The patch may, for instance, have a relatively thin and flexible form that conforms to the contours of skin. The patch may, for example, include an adhesive, for instance, a bio-compatible pressure sensitive adhesive to removably secure the patch to the skin with the microneedles in contact with the skin. Thus, the adhesive may overlie the microneedles. The patch may additionally include a selectively removable release liner to cover the pressure sensitive adhesive prior to use. The device may be supplied or sold in sterile packaging. The device may be supplied with one or more cosmetic, cosmeceutical, nutraceutical, and/or pharmaceutical compositions or formulations pre-applied or preloaded to or in the device and/or microneedles. Alternatively or additionally, the device may be supplied as part of a kit, along with a receptacle or reservoir (e.g., squeeze tube, vial, jar, foil package) that contains one or more cosmetic, cosmeceutical, nutraceutical, and/or pharmaceutical compositions or formulations, and/or written instructions for using the device and/or cosmetic, cosmeceutical, nutraceutical, and/or pharmaceutical composition(s) or formulation(s). Thus, the cosmetic, cosmeceutical, nutraceutical, and/or pharmaceutical composition(s) or formulation(s) may be applied or loaded to or in the device just prior to use, after removal of the device from its packaging. For example, an end consumer, physician, cosmetologist or other may apply or load the cosmetic, cosmeceutical, nutraceutical, and/or pharmaceutical composition(s) or formulation(s).

Behavioral elSkin—"a Day in the Life"

Vice-president of merchandizing for Costco, Barbara Hornsby wakes in her condo on the Upper East Side, it is 6:15 AM and her iPhone 6 is playing WNYC. She pushes the off button with distain. Barbara is definitely not a morning person. A busy day is ahead with multiple meetings and a quarterly sales review with the CEO. She pulls on her white silk robe and heads to the kitchen. She makes Earl Grey tea, adds half and half and sits down to read the mail and New York Times that her amazing husband has lovingly laid out for her on the kitchen counter. It is now 6:45 AM and time to move to the bathroom for the daily routine. She showers quickly with no time for hair, dries off with a large white towel from Lord and Taylor and heads over to her makeup table and takes a seat.

At 57 years of age Barbara has a very youthful appearance. Some mistake her for being in her 40s but given her Nordic heritage (blue eyes and fair skin), it has taken a good deal of personal care and many skin care products over the years to maintain this young-looking appearance so critical to her profession. Opening her makeup table drawer she removes an elSkin patch from the manufacturer's protective pouch. Made of thin and flexible silicon, it is about half an inch wide and about two inches long. Barbara carefully places it (just like a bandage) on her forehead, just above her artfully waxed eyebrows—the wrinkle zone. She removes a plastic strip from the back of the elSkin and there is an immediate tingling, rather pleasant like sun on a warm summer's day—this lets Barbara know elSkin is working to:

Diminish the appearance of fine lines and wrinkles;
Enhance the production of healthy, new, radiant skin;
Hydrate skin so it's more plump, firm and healthy; and
Reduce the appearance of dark spots and hyperpigmentation.

When she first bought the product Barbara read the manufacture's explanation on how elSkin works. It has a user-activated in situ battery that forms an electric current using an array of microneedles. She recalls they are very carefully manufactured in a lab and they are only about 750 microns long, tapering to around 30 microns. They are made of chitin, similar to the exoskeletons of arthropods such as crustaceans, e.g., crabs, lobsters, shrimps and some insects. Its biodegradability means it wears away with time as the skin heals. Dosed with FDA approved skin care pharmaceuticals the microneedles penetrate the upper layers of the skin to deliver a specific dose of skin care product precision driven by the electric current. This is far superior in performance to other skin care products that are just placed topically on the skin; Barbara has long discarded these (to the cast-off skin care cream box of expensive disappointments) as they were not very effective.

She begins to work on her eye makeup. After four minutes the elSkin tingling has largely stopped and she removes the elSkin rectangle from her forehead. Barbara looks carefully in the incandescent light illuminated makeup mirror—turning her head from left to right and back looking for telltale shadows of wrinkles on her forehead, she sees none. A knowing smiles forms on her face. elSkin is an amazing product and worth every dollar and cent.

Barbara proceeds to complete her face makeup, puts on a two-piece black power dress, a pair of Diaz black leather low-heel booties with bright red sole (Manolo Blahniks today), a last look in the mirror, a sip of now cold tea, and out the door to the landing.

She takes the elevator to the lobby. On the way down she looks in the elevator mirror and notices how smooth her forehead is thanks to elSkin. A smile forms on her youthful face—elSkin is working, and it is going to be a very good day!

BRIEF DESCRIPTION OF THE SEVERAL VIEWS OF THE DRAWINGS

The patent or application file contains at least one drawing executed in color. Copies of this patent or application publication with color drawing(s) will be provided by the Office upon request and payment of the necessary fee.

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 1 is table showing retail sales of skin care products in the United States in 2014 by Chanel.

DETAILED DESCRIPTION

Figure 2:
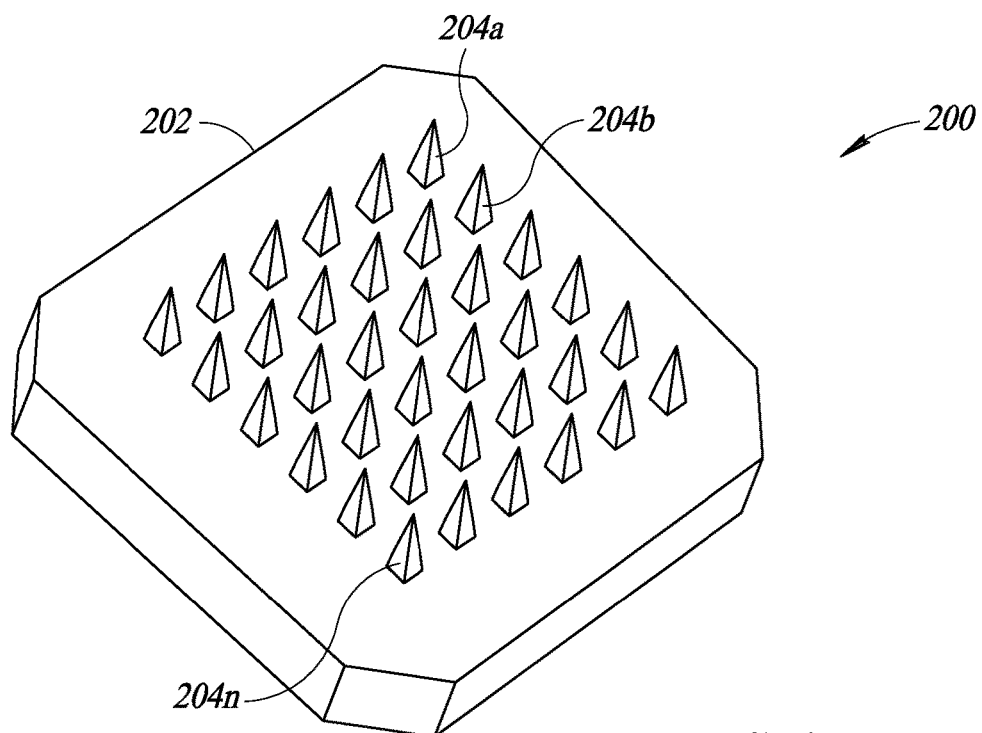
FIG. 2 is a diagram that shows a substrate with a microneedle array, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc.

Unless the context requires otherwise, throughout the specification and claims which follow, the word "comprise" and variations thereof, such as, "comprises" and "comprising" are to be construed in an open, inclusive sense, that is, as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Main Problem Being Addressed

In the year 2016, the global skin care market is estimated to be worth about USD $121 billion.

FIG. 1 shows the retail sales of skin care products in the United States in 2014 by Chanel. In that year, facial anti-aging represents the largest segment at $1,221.9 million in combined markets ("Multi-market") and $486.6 million in direct therapeutics ("Drug").

Anti-aging creams are predominantly moisturizer-based cosmetic pharmaceutical ("cosmeceutical") skin care products marketed with the promise of making the consumer look younger by reducing, masking or preventing signs of skin aging.

These signs are laxity (sagging), rhytids (wrinkles), and photoaging, which includes erythema (redness), dyspigmentation (brown discolorations), solar elastosis (yellowing), keratoses (abnormal growths), and poor texture. Anti-aging creams may also focus on specific causes of skin aging, such as exposure to the sun.

Despite great demand, many anti-aging products and treatments have not been proven to give lasting or major positive effects. One study found that the best performing creams reduced wrinkles by less than 10% over 12 weeks, which is not noticeable to the human eye. Another study found that cheap moisturizers were as effective as high-priced anti-wrinkle creams. However, recent studies at Manchester University showed that some ingredients have an effect.

Traditionally, anti-aging creams have been marketed towards women, but products specifically targeting men are increasingly common. It is worth noting that anti-aging creams may also include conventional moisturizing ingredients.

Cosmetic Formulations

Cosmetic formulations contemplated in this application can include a number of ingredients such as inks, dyes, colorants, fragrances, antioxidants, skin hydrating agents, skin emollients, humectants, moisturizers, permeation enhancers, fillers, or any suitable combination of the foregoing.

Cosmetic compositions which may be employed also include, but are not limited to, one or more of: anti-oxidants; free radical scavengers; moisturizers; depigmentation agents; reflectants; humectants; anti-aging agents; anti-wrinkling agents, antiseptics; keratolytic agents; fresheners; healing agents; peptides, polypeptides and proteins; deodorants and antiperspirants; skin emollients and skin moisturizers; tanning agents; skin lightening agents; depilating agents; make-up preparations; vitamins; amino acids and their derivatives; herbal extracts; retinoids; flavoids; sensory markers (i.e., cooling agents, heating agents, etc.); skin conditioners; chelating agents; coloring agents; sunscreens; nourishing agents; moisture absorbers; sebum absorbers and the like; and mixtures thereof.

The following provides illustrative example of cosmetic agents suitable for use in particular embodiments described herein.

Antioxidants

Illustrative examples of free radical scavengers or antioxidants include, but are not limited to, polyphenols, carotenoids, flavonoids, vitamin E, ubiquinones, glutathione, uric acid, superoxide dismutase, $\alpha$-lipoic acid, licorice extract, rosemary extract and derivatives thereof, Coenzyme Q10, ascorbic acid, lipoic acid, hydroquinones, and soy isoflavones. One having skill in the art would appreciate that a combination of antioxidants is more effective than a single antioxidant on an equal weight basis due to antioxidant cascade mechanism.

Further illustrative examples include rutin (flavone), quercetin (flavone), hesperidin (flavone), diosmin (flavone), mangiferin (xanthone), mangostin (xanthone), cyanidin (carotenoid), astaxanthin (carotenoid), xanthophyll (carotenoid), lycopene (carotenoid), carotene (carotenoid), resveratrol, (polyphenol), tetrahydrocurcumin (polyphenol), rosmarinic acid (polyphenol), ellagic acid (polyphenol), hypericin (polyphenol), chlorogenic acid (polyphenol), oleuropein (polyphenol), lipoic acid (disulfide), glutathione-oxidized (disulfide), cystine (disulfide), N-acetyl-cystine (disulfide), glutathione-reduced (sulfhydryl), cystein (sulfhydryl), and N-acetyl-cysteine (sulfhydryl).

Skin Hydrating Agents

Skin hydrating agents suitable for use with the described device include glycerol, propylene glycol, polyalcohols, hyaluronic acid, sorbitol and sorbitol derivatives, glycerin, ethylene glycol, polyethylene glycol, polypropylene glycol, 1,3-butane diol, hexylene glycol, isoprene glycol, xylitol, fructose and mixtures thereof.

Emollients

The function of the emollients in cosmetic compositions is to add or replace natural oils to the skin, trying to keep the integrity of the hydrolipidic mantle of the skin. They can also act as solubilizers of sunscreens.

Illustrative examples of emollients include petroleum gel, petrolatum, mineral oil, lanolin, vegetable oils, dimethicone, dimethicone copolyol, cationic monomers and polymers, isostearyl isostearate, glyceryl laurate, methyl gluceth 10, methyl gluceth 20 chitosan, and mixtures thereof.

Further, illustrative examples of emollients comprising conventional lipids, include, but are not limited to, for example, oils, waxes and other water-insoluble components and polar lipids, which are those modified so as to increase their solubility in water by esterification of a lipid to a hydrophilic unit like, for example, hydroxyl groups, carbonyl groups, among others. Some components that may be used as emollients are natural oils derived from plants, esters, silicone oils, polyunsaturated fatty acids, lanoline and derivatives thereof. Some natural oils that may be used are derived from apricot kernels, sesame seeds, soybeans, groundnut, coconut, olive, cacao butter, almond, carnauba, cotton seed, rice bran, peach stone, mango stone, jojoba, macadamia, coffee bean, grape seed, pumpkin seed, among others and mixtures thereof.

Some ethers and esters may also be used in the function of emollients, such as carboxylic acid C9-C30 alkyl ester, C0-C6 diol monoesters and C8-C30 carboxylic acid diesters, C10-C20 alcohol sucrose monoesters and combinations thereof. Examples of these compounds are: dicaprylic ether, isopropyl palmitate, dicaprylyl carbonate, C12-C15 alkyl benzoate, isopropyl isononate, sucrose palmitate, sucrose oleate, isostearyl lactate, glyceryl behenate, triglycerol-4 isostearate, lauryl pirrolidone carboxylic acid, pantenyl triacetate, and combinations thereof.

Other fatty alcohols, mono-, di- or triglyceride ethers that have a lipophilic nature such as dicaprylylic ether may be used, in addition to synthetic and natural hydrocarbons, organic carbonates such as dicaprylyl carbonate, some types of silicones like cyclomethicone, and mixtures thereof.

In addition, various natural compounds may be used as emollients such as, for example, microcrystalized wax, carnauba wax, cupuassu wax, bee wax, ozokerite wax, among others.

Other illustrative examples of moisturizers include: alpha hydroxy acid, glycosaminoglycan, grape seed oil, cranberry seed oil, green tea, white tea, methylparaben, propylparaben, caffeine, xanthine, vitamin B-3, nicotinamide, licorice, calamine, aluminum hydroxide gel, aloe, lanolin, glycerin, vitamin E, vitamin E acetate, farnesol, glycyrrhetinic acid, propylene glycol, ethylene glycol, triethylene glycol, hard fat, kaolin, lanolin, mineral oil, petrolatum, topical starch, white petroleum, cod liver oil, shark liver oil, zinc oxide, or a combination thereof.

Additional suitable topical moisturizers are disclosed in U.S. Pat. Nos. 6,096,334; 6,096,033; 5,741,510; 5,536,263; 4,675,009; 4,307,717; 4,274,420; 5,976,565; 5,536,263; and references cited therein.

Keratolytic Agents

Illustrative examples of keratolytic agents include, but are not limited to, salicylic acid, benzoyl peroxide, sulphur, retinoic acid, and any of a number of fruit acids and alpha hydroxy acids.

Alpha-Hydroxy Acids

Illustrative examples of suitable alpha-hydroxy acids (AHAs) can be used with or in the described device or patch as exfoliants, moisturizers, and emollients. Lactic acid salts can be used with or in the described device or patch, such as sodium lactate, and can be hypothesized to be part of the skin's own natural moisturizing system. In addition, AHAs and salicylic acid can be used with or in the described device or patch as a structurally similar beta-hydroxy acid as peeling agents. The moisturizing activity of AHAs and their ability to exfoliate the skin and interfere with intercellular cohesion in the outer epidermis is well known. It has been suggested that AHAs interfere with cohesion in the stratum granulosum, unlike salicylic acid and other exfoliants.

Vitamins

Illustrative examples of suitable vitamins include, without limitation, folic acid, vitamin A, vitamin B (all series, including B3, B6, B12), vitamin C, vitamin D, vitamin E, vitamin K, calcium, magnesium, or the like, in order to facilitate treatment of an iron deficiency as described herein. As used herein, the term "vitamin C" means any form of vitamin C, including ascorbate and L threonate. As used herein, the term "vitamin D" means both cholecalciferol (vitamin D3) and ergocalciferol (vitamin D2). As used herein, the term "vitamin E" means alpha-tocopherol, D-alpha-tocopherol, D-alpha-tocopheryl succinate (or acetate), DL-alpha-tocopherol, DL-alpha-tocopheryl acetate (or succinate), gamma tocopherol, mixed tocopherols, and DL-alpha tocopherol nicotinate. As used herein, the term "calcium" means any form of calcium including calcium carbonate, phosphate, lactate, gluconate, citrate and combinations thereof. As used herein, the term "magnesium" means any form of magnesium, including magnesium oxide, magnesium chloride, magnesium lactate, and magnesium sulphate and magnesium gluconate.

Vitamin C promotes collagen (connective tissue) synthesis, lipid (fat) and carbohydrate metabolism, and the synthesis of neurotransmitters. It is also essential for optimum maintenance of the immune system. Vitamin C is toxic to a wide range of cancer cells, especially melanoma. The oxidizing enzyme tyrosine that catalyzes the aerobic action of tyrosine into melanin and other pigments is also inhibited by the presence of vitamin C. Vitamin C has been found to be effective in catalyzing the immune response to many viral and bacterial infections. Besides the many applicable uses set forth above, vitamin C is essential for collagen synthesis and wound healing.

Amino Acids

Illustrative examples of amino acid agents include, but are not limited to, amino acids derived from the hydrolysis of various proteins as well as the salts, esters, and acyl derivatives thereof. Examples of such amino acid agents include amphoteric amino acids such as alkylamido alkylamines; stearyl acetyl glutamate; capryloyl silk amino acid; capryloyl collagen amino acids; capryloyl kertain amino acids; capryloyl pea amino acids; cocodimonium hydroxypropyl silk amino acids; corn gluten amino acids; cysteine; glutamic acid; glycine; hair keratin amino acids; hair amino acids such as aspartic acid, threonine, serine, glutamic acid, proline, glycine, alanine, half-cystine, valine, methionine, isoleucine, leucine, tyrosine, phenylalanine, cysteic acid, lysine, histidine, arginine, cysteine, tryptophan, and citrulline; lysine; silk amino acids; wheat amino acids; and mixtures thereof.

Polypeptides

Illustrative examples of peptides, polypeptides, and proteins include those polymers that have a long chain, such as at least about 10 carbon atoms, and a high molecular weight, such as at least about 1000, and are formed by self-condensation of amino acids. Examples of such proteins include collagen; deoxyribonuclease; iodized corn protein; keratin; milk protein; protease; serum protein; silk; sweet almond protein; wheat germ protein; wheat protein; alpha and beta helix of keratin proteins; and hair proteins, such as intermediate filament proteins, high-sulphur proteins, ultra-high-sulphur proteins, intermediate filament-associated proteins, high-tyrosine proteins, high-glycine tyrosine proteins, tricohyalin, and mixtures thereof.

Sunscreen Agents

Illustrative examples of sunscreen agents include, but are not limited to, butyl methoxydibenzoylmethane, octyl methoxycinnamate, oxybenzone, octocrylene, octyl salicylate, phenylbenzimidazole sulfonic acid, ethyl hydroxypropyl aminobenzoate, menthyl anthranilate, aminobenzoic acid, cinoxate, diethanolamine methoxycinnamate, glyceryl aminobenzoate, titanium dioxide, zinc oxide, oxybenzone, padimate O, red petrolatum, and mixtures thereof. An example of a suitable tanning agent that can be used with or in the described device or patch is dihydroxyacetone.

Depilating Agents

Illustrative examples of depilating agents include calcium thioglycolate, magnesium thioglycolate, potassium thioglycolate, strontium thioglycolate, and mixtures thereof.

Antiperspirant

Illustrative examples of antiperspirants and deodorants include aluminium chlorohydrates, aluminium zirconium chlorohydrates, and mixtures thereof.

Surfactants

Illustrative examples of surfactants include, but are not limited to, those selected from the anionic, cationic, nonionic, amphoteric, zwitterionic, and combinations thereof. Most preferred are nonionic and amphoteric surfactants due to their mildness. Examples of suitable amphoterics are cocoamidopropylbetaine and lauroamphoacetate. Examples of suitable nonionics are dialkylamine oxides, alkyl polyglycosides and methyl glucamides. Examples of mild anionic surfactants include salts of sarcosinate, taurate, and cocoyl isethionate. Other surfactants that can be used with or in the described device or patch are sucrose distearate, diglyceryldistearate, tetraglyceryl tristearate, decaglyceryl decastearate, diglyceryl monostearate, hexaglyceyl tristearate, decaglyceryl pentastearate, sorbitan monostearate, sorbitan tristearate, diethylene glycol monostearate, the ester of glycerol and of palmitic acid and stearic acid, monostearate polyoxyethylenated with 2 OE (containing 2 oxyethylene units), glyceryl mono- and dibehenate, and pentaerythrityl tetrastearate.

Pharmaceutical Compositions

In particular embodiments, the electroactive microneedles can be combined with pharmaceutical compositions that comprise one or more of: anti-oxidants; free radical scavengers; moisturizers; skin hydrating agents; depigmentation agents; reflectants; humectants; anti-aging agents; anti-wrinkling agents; antiseptics; keratolytic agents; fresheners; healing agents; peptides, polypeptides and proteins; deodorants and antiperspirants; skin emollients and skin moisturizers; tanning agents; skin lightening agents; depilating agents; make-up preparations; vitamins; amino acids and their derivatives; herbal extracts; retinoids; flavoids; sensory markers (i.e., cooling agents, heating agents, etc.); skin conditioners; chelating agents; coloring agents; sunscreens; nourishing agents; moisture absorbers; sebum absorbers and the like, and mixtures thereof, as discussed elsewhere herein.

Dermatological Conditions

Illustrative examples of dermatological diseases, disorders, and conditions include, but are not limited to: acne; bacterial skin infections including, but not limited to, cellulitis, erysipelas, erythrasma, folliculitis and skin abscesses, hidradenitis suppurativa, impetigo, lymphadenitis, lymphangitis, necrotizing skin infections, staphylococcal scalded skin syndrome; blistering diseases including, but not limited to, bullous pemphigoid, dermatitis herpetiformis, and pemphigus vulgaris; fungal skin infections including, but not limited to, candidiasis, ringworm (tinea), athlete's foot, jock itch, scalp ringworm, body ringworm, and beard ringworm; hair disorders including, but not limited to, alopecia, hirsutism and hypertrichosis, and ingrown hairs; itching and noninfectious rashes including, but not limited to, dermatitis, contact dermatitis, atopic dermatitis, seborrheic dermatitis, nummular dermatitis, generalized exfoliative dermatitis, stasis dermatitis, localized scratch dermatitis, perioral dermatitis, pompholyx, drug rashes, erythema multiforme, erythema nodosum, granuloma annulare, itching, keratosis pilaris, lichen planus, pityriasis rosea, psoriasis, rosacea, Stevens-Johnson Syndrome (SJS) and toxic epidermal necrolysis; nail disorders including, but not limited to, deformities and discoloration, deformities associated with skin diseases, infections, onychomycosis, paronychia, chronic paronychia, green nail syndrome, verruca vulgaris, and ingrown toenail; noncancerous skin growths including, but not limited to, dermatofibromas, epidermal cysts; growths and malformations of the vessels including, but not limited to, hemangiomas, port-wine stain, lymphangiomas, pyogenic granulomas, spider angiomas, keloids, keratoacanthomas, lipomas, moles, seborrheic keratoses, skin tags; parasitic skin infections including, but not limited to, cutaneous larva migrans, cutaneous myiasis, lice infestation, and scabies; pigment disorders including, but not limited to, albinism, melasma, and vitiligo; pressure sores; skin cancers including, but not limited to, basal cell carcinoma, Kaposi's sarcoma, melanoma, Paget's disease of the nipple, and squamous cell carcinoma; sunlight and skin damage including, but not limited to, photosensitivity reactions, and sunburn; sweating disorders including, but not limited to, diminished sweating, excessive sweating, and prickly heat; viral skin infections including, but not limited to, molluscum contagiosum, and warts.

In various embodiments, a pharmaceutical composition comprises an effective amount of one or more agents to treat and/or prevent a dermatological disease, disorder, or condition comprising one or more antimicrobial (e.g., antibacterial) agents; allergy inhibitors; anti-acne agents; analgesics; antitussives; antipruritics; local anesthetics; anti-hair loss agents; hair growth promoting agents; hair growth inhibitor agents, antihistamines; keratolytic agents; anti-inflammatory agents; anti infectives; anti-cancer agents; inflammation inhibitors; anticholinergics; vasoconstrictors; vasodilators; wound healing promoters; peptides, polypeptides and proteins; antifungals such as antifungals for foot preparations; external analgesics; counterirritants; hemorrhoidals; insecticides; poison ivy products; poison oak products; burn products; anti-diaper rash agents; prickly heat agents; sensory markers (i.e., cooling agents, heating agents, etc.); cell turnover enhancers; anesthetics; immunomodulators; fillers; and the like, as discussed elsewhere herein.

In various embodiments, a pharmaceutical composition provided to treat or prevent a dermatological disease or disorder via application by the device comprises one or more cosmetic, dermatological, and pharmaceutical active ingredients that have an effect on the skin, including, but not limited to: anti-oxidants; free radical scavengers; moisturizers; depigmentation agents; reflectants; humectants; antimicrobial (e.g., antibacterial) agents; allergy inhibitors; anti-acne agents; anti-aging agents; anti-wrinkling agents, antiseptics; analgesics; antitussives; antipruritics; local anesthetics; anti-hair loss agents; hair growth promoting agents; hair growth inhibitor agents; antihistamines; keratolytic agents; anti-inflammatory agents; fresheners; healing agents; anti-infectives; inflammation inhibitors; anticholinergics; vasoconstrictors; vasodilators; wound healing promoters; peptides, polypeptides and proteins; deodorants and antiperspirants; skin emollients and skin moisturizers; hair conditioners; hair softeners; hair moisturizers; tanning agents; skin lightening agents; antifungals such as antifungals for foot preparations; depilating agents; external analgesics; counterirritants; hemorrhoidals; insecticides; poison ivy products; poison oak products; burn products; anti-diaper rash agents; prickly heat agents; make-up preparations; vitamins; amino acids and their derivatives; herbal extracts; retinoids; flavoids; sensory markers (i.e., cooling agents, heating agents, etc.); skin conditioners; hair lighteners; chelating agents; cell turnover enhancers; coloring agents; sunscreens; anesthetics; immunomodulators and nourishing agents; moisture absorbers; sebum absorbers and the like, and mixtures thereof.

In a particular embodiment, a pharmaceutical composition provided to treat or prevent a dermatological disease or disorder comprises one or more of steroid hormones, preferably estradiol either alone or combined with other drugs, which can be applied on long-term wounds, for instance, crural ulcera, for the treatment of wounds.

Antibiotics

In another particular embodiment, a pharmaceutical composition provided to treat or prevent a dermatological disease or disorder comprises one or more antibacterial agents including, but not limited to, penicillins, cephalosporins, other beta-lactam compounds, aminoglycosides, bacitracin, tetracycline, doxycycline, minocycline, erythromycin, neomycin, tetracycline, chlortetracycline, benzethonium chloride, phenol, and mixtures thereof.

Insecticides

In another particular embodiment, a pharmaceutical composition provided to treat or prevent a dermatological disease or disorder comprises one or more insecticides (including insect repellents, anti-scabies and anti-lice treatments) including, but not limited to, permethrin, pyrethrin, piperonyl butoxide, imidacloprid, and N,N-diethyl toluamide, which refers to the material containing predominantly the meta isomer.

Anti-Acne Agents

Illustrative examples of anti-acne agents include, but are not limited to, salicylic acid, benzoyl peroxide, sulphur, retinoic acid, fruit acids, alpha hydoxy acids, clindamycin, erythromycin, resorcinol, sulfur, tretinoin, adapalene, azelaic acid, tazarotene, doxycycline, minocycline, and isotretinoin.

Whitening Agents

Illustrative examples of skin whitening agents, include, but are not limited to, substances for whitening of the skin, lightening of the skin, spots prevention or treatment of spots, e.g., hydroquinone, tretinoin, topical steroids, azelaic acid, kojic acid, arbutin, luteolin, licorice, and extracts containing these substances. Arbutin and luteolin and extracts containing these substances are preferred.

Anti-Fungal Agents

In another particular embodiment, a pharmaceutical composition provided to treat or prevent a dermatological disease or disorder comprises one or more anti-fungal agents including, but not limited to, tolnaftate.

Analgesics

In another particular embodiment, a pharmaceutical composition provided to treat or prevent a dermatological disease or disorder comprises one or more external analgesics and local anesthetics, including, but not limited to, benzocaine, dibucaine, benzyl alcohol, camphor, capsaicin, capsicum, capsicum oleoresin, juniper tar, menthol, methyl nicotinate, methyl salicylate, phenol, resorcinol, turpentine oil, and mixtures thereof.

Counterirritants

In another particular embodiment, a pharmaceutical composition provided to treat or prevent a dermatological disease or disorder comprises one or more counterirritants including, but not limited to, camphor, menthol, methyl salicylate, peppermint oil, clove oil, ichtammol, and mixtures thereof.

Inflammation Inhibitors

In another particular embodiment, a pharmaceutical composition provided to treat or prevent a dermatological disease or disorder comprises one or more inflammation inhibitors including, but not limited to, hydrocortisone.

Hemorrhoidal Products

In another particular embodiment, a pharmaceutical composition provided to treat or prevent a dermatological disease or disorder comprises one or more hemorrhoidal products including, but not limited to, anesthetics such as benzocaine, pramoxine hydrochloride, and mixtures thereof antiseptics such as benzethonium chloride; astringents such as zinc oxide, bismuth subgallate, balsam Peru, and mixtures thereof skin protectants such as cod liver oil, vegetable oil, and mixtures thereof.

Therapeutic Agents

In another particular embodiment, a pharmaceutical composition provided to treat or prevent a dermatological disease or disorder comprises one or more therapeutic agents that are effective in the treatment of dandruff, seborrheic dermatitis, and psoriasis, as well as the symptoms associated therewith. Examples of such suitable therapeutic agents include, but are not limited to, zinc pyrithione, shale oil and derivatives thereof such as sulfonated shale oil, selenium sulfide, sulfur; salicylic acid; coal tar; povidone-iodine and imidazoles.

Antiseptics

In another particular embodiment, a pharmaceutical composition provided to treat or prevent a dermatological disease or disorder comprises one or more antiseptics including, but not limited to, triclosan (Irgasan DP 300), phenoxy isopropanol, resorcinol, chlorhexidine, povidone, and iodine.

Anti-Irritants

In another particular embodiment, a pharmaceutical composition provided to treat or prevent a dermatological disease or disorder comprises one or more anti-irritants including, but not limited to, alpha-bisabolol, famesol, chamomile extract and glycyrrhetinic acid.

Anti-Inflammatory Analgesic Agents

In another particular embodiment, a pharmaceutical composition provided to treat or prevent a dermatological disease or disorder comprises one or more anti-inflammatory analgesic agents including, but not limited to, acetaminophen, methyl salicylate, monoglycol salicylate, aspirin, mefenamic acid, flufenamic acid, indomethacin, diclofenac, alclofenac, diclofenac sodium, ibuprofen, ketoprofen, naproxen, pranoprofen, fenoprofen, sulindac, fenclofenac, clidanac, flurbiprofen, fentiazac, bufexarnac, piroxicam, phenylbutazone, oxyphenbutazone, clofezone, pentazocine, mepirizole, tiaramide hydrochloride, and the like. Examples of steroidal anti-inflammatory agents include, but are not limited to, hydrocortisone, predonisolone, dexamethasone, triamcinolone acetonide, fluocinolone acetonide, hydrocortisone acetate, predonisolone acetate, methylpredonisolone, dexamethasone acetate, betamethasone, betamethasone valerate, flumetasone, fluorometholone, beclomethasone diprionate, and the like.

Antihistamines

In another particular embodiment, a pharmaceutical composition provided to treat or prevent a dermatological disease or disorder comprises one or more antihistamines including, but not limited to, diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, and the like. Examples of local anesthetics include, but are not limited to, dibucaine hydrochloride, dibucaine, lidocaine hydrochloride, lidocaine, benzocaine, p-buthylaminobenzoic acid 2-(die-ethylamino) ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine, dyclonine hydrochloride, and the like.

Bactericides and Disinfectants

In another particular embodiment, a pharmaceutical composition provided to treat or prevent a dermatological disease or disorder comprises one or more bactericides and disinfectants including, but not limited to, thimerosal, phenol, thymol, benzalkonium chloride, benzethonium chloride, chlorhexidine, povidone iode, cetylpyridinium chloride, eugenol, trimethylammonium bromide, and the like. Examples of vasoconstrictors include, but are not limited to, naphazoline nitrate, tetrahydrozoline hydrochloride, oxymetazoline hydrochloride, phenylephrine hydrochloride, tramazoline hydrochloride, and the like. Examples of hemostatics include, but are not limited to, thrombin, phytonadione, protamine sulfate, aminocaproic acid, tranexamic acid, carbazochrome, carbaxochrome sodium sulfanate, rutin, hesperidin, and the like.

Chemotherapeutic Drugs

In another particular embodiment, a pharmaceutical composition provided to treat or prevent a dermatological disease or disorder comprises one or more chemotherapeutic drugs including, but not limited to, sulfamine, sulfathiazole, sulfadiazine, homosulfamine, sulfisoxazole, sulfisomidine, sulfamethizole, nitrofurazone, and the like. Examples of antibiotics that can be used with or in the described device or patch include penicillin, meticillin, oxacillin, cefalotin, cefalordin, erythromcycin, lincomycin, tetracycline, chlortetracycline, oxytetracycline, metacycline, chloramphenicol, kanamycin, streptomycin, gentamicin, bacitracin, cycloserine, and the like.

Antiviral Drugs

In another particular embodiment, a pharmaceutical composition provided to treat or prevent a dermatological disease or disorder comprises one or more antiviral drugs including, but not limited to, protease inhibitors, thymadine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir.

Natural Extracts

In another particular embodiment, a pharmaceutical composition provided to treat or prevent a dermatological disease or disorder comprises vegetable preparations, such as extracts or tinctures for the treatment of topical skin diseases. Suitable extracts or tinctures include oak bark extract, walnut extract, tincture of arnica, hamamelis extract, ribwort extract, pansy extract, thyme or sage extract; for the treatment of damaged or injured skin, for example, St. John's Wort tincture, cone flowers tincture, chamomile flowers extract, or calendula flowers tincture; and for the care of exhausted and damaged skin, for example, birch leaves extract, nettle extract, coldsfoot extract, comfrey tincture, horsetail extract, or aloe vera extract. Vegetable preparations can also be released from the film layer for the intradermal treatment of diseases, for example, extracts of horse chestnut and butcher's broom in case of vein diseases, or extracts and tinctures of arnica, calendula, and capsicum in case of contusions, distortions, or hemorrhages. Vegetable preparations in the described device or kit may also be used in transdermal therapy, for example, ginseng extract in case of geriatric complaints; valerian tincture, extracts of Melissa and hop to cause a sedative effect in case of super excitation, sleep disturbances, and stress; extracts of kola and tea to achieve a stimulative effect; or hawthorn extract to stabilize the circulatory system.

Cosmetic Electrotherapy

Cosmetic electrotherapy is a range of beauty treatments that uses low electric currents passed through the skin to produce several therapeutic effects such as muscle toning in the body and micro-lifting of the face. It is based on electrotherapy, which has been researched and accepted in the field of rehabilitation, though the "scientific and medical communities have tended to sideline or dismiss the use of electrotherapy for healthy muscles". Such can be advantageously accomplished via a device with in situ anode and cathode microneedles, either with or without any cosmetic, cosmeceutical, nutraceutical, and/or pharmaceutical composition or formulation. The in situ anode and cathode microneedles form battery cells or half-cells when placed in contact with an electrolyte found in bodily interface tissue, to produce an electromotive force without any additional chemical battery or power source. The microneedles may be composed of, or may carry (e.g., coated with) electrical potential material(s) that has or have an electrical potential relative to an electrolyte in the bodily interface material. A first number of microneedles may, for instance, include a first electrical potential material having a first electrical potential. A second number of microneedles may, for instance, include a second electrical potential material having a second electrical potential. The first number of microneedles may thus serve as an anode, while the second number of microneedles may thus server as a cathode. Alternatively, a number of microneedles may, for instance, include a both a first electrical potential material and a second electrical potential material, having a first electrical potential and a second electrical potential, respectively. Respective portions of each of the microneedles may thus serve as an anode and a cathode. Again, such may be accomplished without any other or additional electrochemical battery.

The use of electricity in cosmetics goes back to the end of the 19th century; almost a hundred years after Luigi Galvani discovered that electricity can make the muscle in a frog's leg twitch (galvanism). Subsequent research in electrophysiology has been carried out by people such as Robert O. Becker; Dr. Björn Nordenström, a former chair of the Nobel Selection Committee for Medicine; and Dr. Thomas Wing, who invented some of the first micro-current devices.

Drug Delivery

A drug, broadly speaking, is any substance that, when absorbed into the body of a living organism, alters normal bodily function. There is no single, precise definition, as there are different meanings in drug control law, government regulations, medicine, and colloquial usage. In pharmacology, a drug is "a chemical substance used in the treatment, cure, prevention, or diagnosis of disease or used to otherwise enhance physical or mental well-being." Drugs may be prescribed for a limited duration, or on a regular basis for chronic disorders.

Drug delivery is the method or process of administering a pharmaceutical compound to achieve a therapeutic effect in humans or animals. Drug delivery technologies modify drug release profile, absorption, distribution and elimination for the benefit of improving product efficacy and safety, as well as patient convenience and compliance. Drug release is from: diffusion, degradation, swelling, and affinity-based mechanisms. Most common routes of administration include the preferred non-invasive peroral (through the mouth), topical (skin), transmucosal (nasal, buccal/sublingual, vaginal, ocular and rectal) and inhalation routes. Many medications, such as peptide- and protein-, antibody-, vaccine- and gene-based drugs, in general may not be delivered using these routes because they might be susceptible to enzymatic degradation, or cannot be absorbed into the systemic circulation efficiently enough, due to molecular size and charge issues, to be therapeutically effective. For this reason many protein and peptide drugs have to be delivered by injection or a nanoneedle array. For example, many immunizations are based on the delivery of protein drugs, and are often done by injection.

Microneedles combine the transdermal delivery capabilities of hypodermic needles with the advantages of dermal patches. Upon insertion, microneedles create small holes in the stratum corneum, the outermost skin layer, to afford improved drug diffusion into the dermis, similarly to hypodermic needles. At the same time, application of microneedles is safe and relatively painless, like dermal patches. Microneedles have the potential to intradermally deliver diagnostic antigens, therapeutics and vaccines. Examples include insulin, other hormones, DNA, Bacillus Calmette-Guérin (BCG), and influenza. Intradermal delivery has been used in diagnostic tests for allergies and tuberculosis (TB). This intradermal delivery is difficult to achieve with hypodermic needles, and requires trained personnel. Coated microneedles are ideally suited for precise intradermal delivery in easy-to-use therapeutics and diagnostics.

Microneedles are made with silicon, metals, synthetic polymers, and, most recently, natural biomaterials such as silk, carboxymethylcellulose ("CMC"), and chitosan. Silicon and metal microneedles offer high elastic modulus and tensile strength to ensure skin penetration. These microneedles are usually coated with the substance that needs to be delivered, or fabricated with an opening for delivery that mimics a traditional hypodermic needle. Polymer microneedles can be made via replica molding of a rigid microneedle master, such as metal, with lower manufacturing costs. Dissolvable and biodegradable polymer microneedles afford the time-delayed or controlled-release delivery of vaccines and therapeutics. Polymers with high elastic modulus and tensile strength are required for successful insertion of the microneedles into the skin. Among these polymers, biodegradable materials are particularly desirable. Chitin [poly($\beta$-(1,4)-N-acetyl-D-glucosamine] is a naturally abundant polysaccharide, which is mechanically robust, nontoxic, physiologically inert, and biodegradable. Chitosan is a linear polysaccharide composed of randomly distributed $\beta$-(1-4)-linked D-glucosamine (deacetylated unit) and N-acetyl-D-glucosamine (acetylated unit). It is made by treating shrimp and other crustacean shells with the alkali sodium hydroxide (NaOH). Research has recently demonstrated that chitin microstructures and nanostructures are easily fabricated with replica molding and micro-contact printing. These materials are attractive because they have extensively been used in humans in the form of surgical sutures and oral formulations, and they are relatively inexpensive to source.

FIG. 2 shows an exemplary device 200 including a substrate 202 carrying, bearing or having a microneedle array 204, according to one illustrated embodiment.

The mechanism for delivery is not based on diffusion, as it is in other transdermal drug delivery products. Instead, it is based on the temporary mechanical disruption of the skin and the placement of the drug or vaccine within the epidermis, where it can dissolve and more readily reach its site of action.

The drug, in the form of biomolecules, can be encapsulated within the microneedles, which are then inserted into the skin in the same way a drug like nitroglycerine is released into the bloodstream from a patch. The drug and possibly the microneedles dissolve within minutes, releasing the trapped cargo at the intended delivery site. They do not need to be removed, and no dangerous or biohazardous substance is left behind on the skin, as the needles are made of a biodegradable substance.

Hollow microneedles have small channels inside them that enable liquid drug formulations to be directly injected into the intradermal space. Both 3M and Nanopass have hollow microneedles and some of these are FDA and EMEA approved for human use as devices.

In microneedle devices, a small area (the size of a traditional transdermal patch) is covered by tens or hundreds of microneedles 204a, 204b, . . . 204n that pierce only the stratum corneum (the uppermost 50 μm of the skin), thus allowing the drug to bypass this important lipophilic barrier. The tiny needles are constructed in arrays to deliver sufficient amount of drug to the patient for the desired therapeutic response.

As described herein, the microneedles 204a-204n may form battery half-cells or battery cells, each of at least some of the microneedles being carrying, bearing, coated with or formed of one or more materials that have an electrical potential relative to an electrolyte. In one implementation, one or more of the microneedles 204a may be functionalized as an anode, while one or more of the microneedles 204b may be functionalized as a cathode 204b. The cathode microneedles may, for instance, be interspersed with the anode microneedles. For instance, the nearest neighbor to each anode microneedle may be a cathode microneedle, and likewise the nearest neighbor to each cathode microneedle may be an anode microneedle. The next nearest neighbors may have the same electrical potential or polarity. Alternatively, microneedles of a first type (e.g., anode) may be grouped together in a first area or region, while microneedles of a second type (e.g., cathode) may be grouped together in a second area or region, separate from the first area. In some implementations, microneedles of a first type (e.g., anode) may be grouped together in two or more areas or regions where are distinct from two or more areas or regions in which microneedles of a second type (e.g., cathode) are grouped, for instance in a checkerboard fashion with anode type electrodes grouped on black squares and cathode type electrodes grouped on white squares, or vice versa. In some implementations, a first portion of one or more of the microneedles 204n may be functionalized as an anode while a second portion of the microneedle(s) 204n may be functionalized as an anode.

Figure 3:
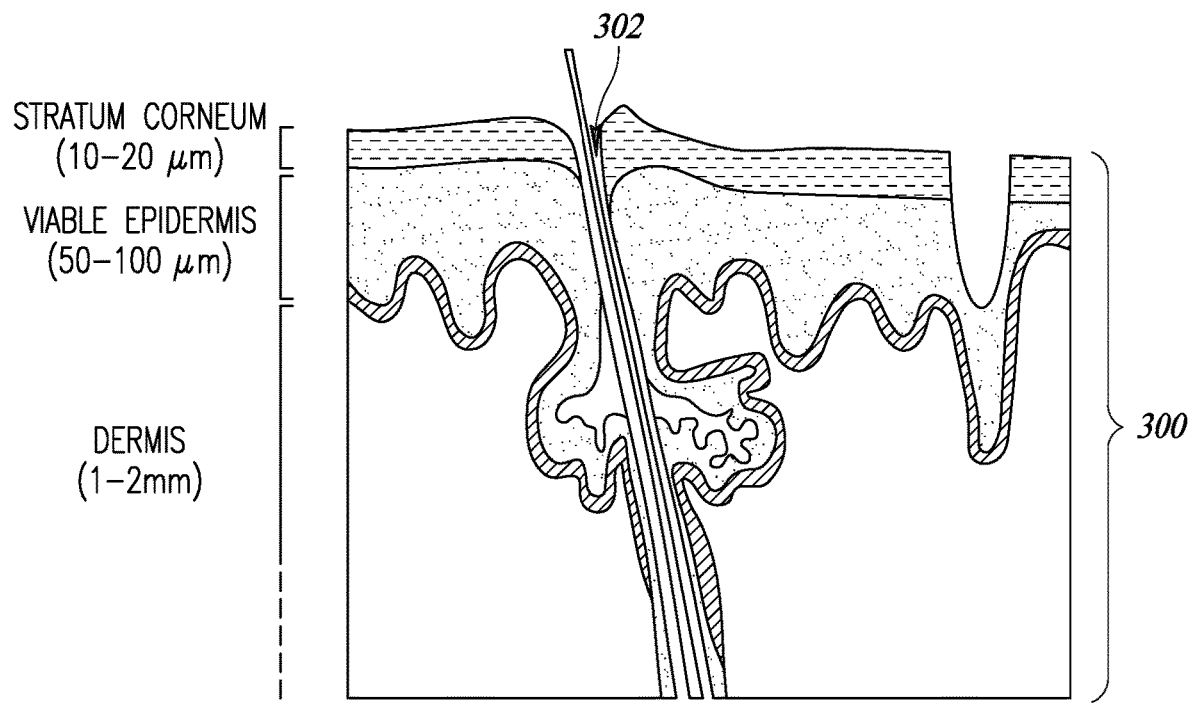
FIG. 3 is cross-sectional diagram showing bodily interface tissue (e.g., skin) subject to treatment via a microneedle, according to one illustrated embodiment.

FIG. 3 shows a cross-section of dermis 300 with a hair follicle 302, the dermis 300 which may be pierced or abraded by one or more microneedles, and subjected to an electromotive force generated by electrical potential material of the microneedles 202 (FIG. 2), according to one illustrated embodiment Delivery Approaches A number of delivery strategies have been employed to use the microneedles for transdermal drug delivery. These include:

Poke with patch approach
Coat and poke approach
Biodegradable microneedles
Hollow microneedles
Dip and scrape "Poke with Patch" Approach This involves piercing an array of solid microneedles into the skin followed by application of the drug patch at the treated site. Transport of drug across skin through the small pores formed by the "poke" can occur by diffusion or possibly by iontophoresis if an electric field is applied.

"Coat and Poke" Approach

In this approach needles are first coated with the drug and then inserted into the skin for drug release by dissolution. The entire drug to be delivered is coated onto the needle itself.

Biodegradable Microneedles

These needles encapsulate the drug within the biodegradable, polymeric matrix, followed by the insertion into the skin and dissolution of the needles for a controlled drug release.

Hollow Microneedles

This involves injecting the drug through the needle with a hollow bore. This approach is more reminiscent of (suggestive of) an injection than a patch.

"Dip and Scrape" Approach

Here microneedles are dipped into a drug solution at the time of application and then scraped across the skin surface to leave behind the drug within the microabrasions created by the needles. The arrays are dipped into a solution of drug and scraped multiple times across the skin to create microabrasions. Unlike microneedles used previously, this study used blunt-tipped microneedles measuring 50-200 µm in length over a 1 $cm^2$ area.

Iontophoresis (a.k.a. Electromotive Drug Administration "EMDA") is a technique using a small electric charge to deliver a medicine or other chemical through the skin. It is basically an injection without the needle. The technical description of this process is a non-invasive method of propelling high concentrations of a charged substance, normally a medication or bioactive agent, transdermally by repulsive electromotive force using a small electrical charge applied to an iontophoretic chamber containing a similarly charged active agent and its vehicle. One or two chambers are filled with a solution containing an active ingredient and its solvent, also called the vehicle. The positively charged chamber, called the anode, will repel a positively charged chemical, whereas the negatively charged chamber, called the cathode, will repel a negatively charged chemical into the skin.

Thin film drug delivery uses a dissolving film or oral drug strip to administer drugs via absorption in the mouth (buccally or sublingually) and/or via the small intestines (enterically). A film is prepared, using hydrophilic polymers, that rapidly dissolves on the tongue or buccal cavity, delivering the drug to the systemic circulation via dissolution when contact with liquid is made.

Thin film drug delivery has emerged as an advanced alternative to the traditional tablets, capsules and liquids often associated with prescription and OTC medications. Similar in size, shape and thickness to a postage stamp, thin film strips are typically designed for oral administration, with the user placing the strip on or under the tongue (sublingual) or along the inside of the cheek (buccal). These drug delivery options allow the medication to bypass the first pass metabolism, thereby making the medication more bioavailable. As the strip dissolves, the drug can enter the blood stream enterically, buccally or sublingually.

The device and kits described herein may incorporate anti-aging ingredients, microneedles and iontophoresis into a multitude of functionalized thin film batteries (using any of a number of manufacturing methods) that enhance the absorption of therapeutic drugs into the skin.

Manufacturing Methods for ElSkin

Figure 4:
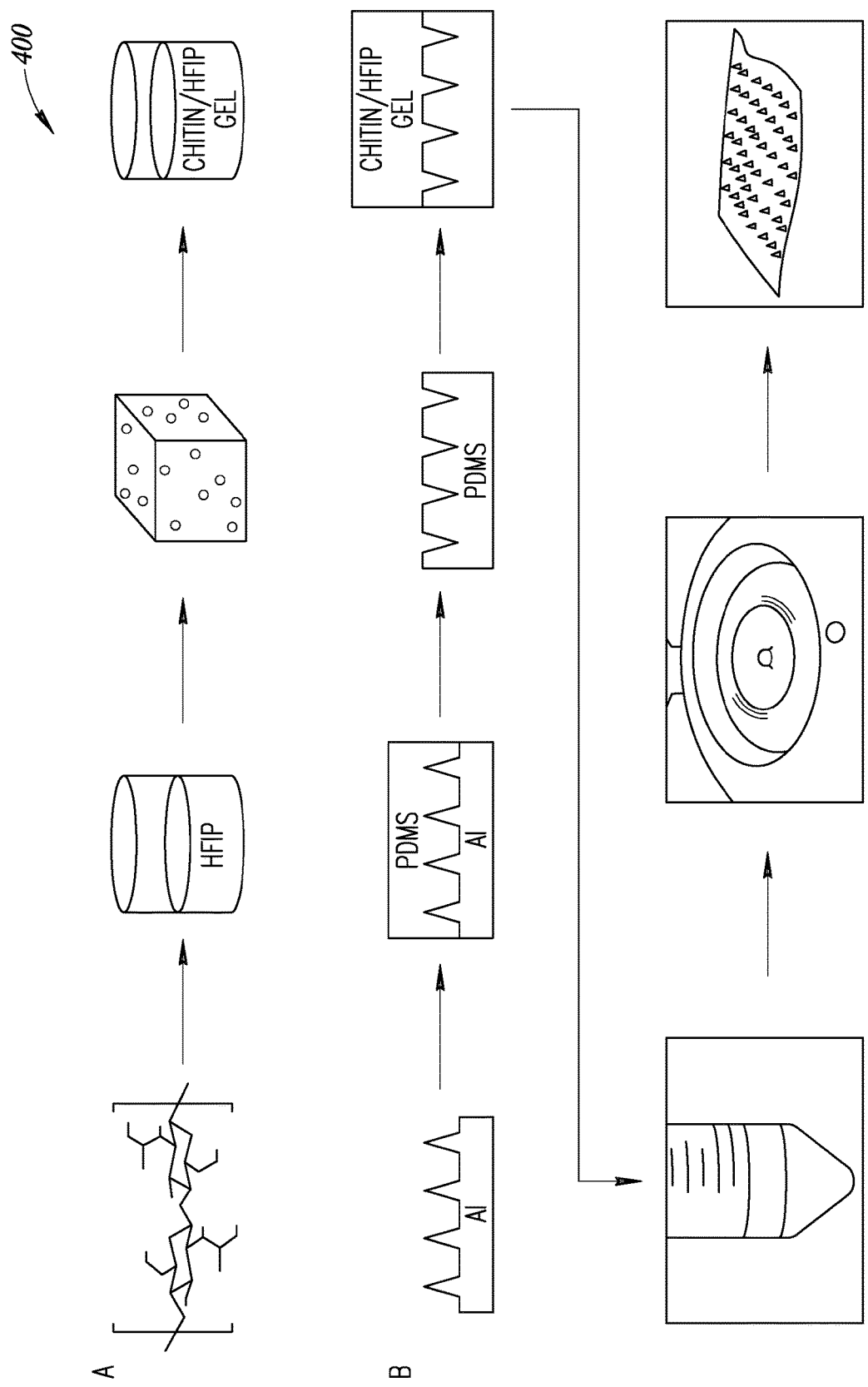
FIG. 4 is a schematic illustration of a method of fabrication of chitin microneedles, according to one illustrated embodiment.

FIG. 4 shows a microneedle fabrication 400, according to one illustrated embodiment.

A battery is a device that converts chemical energy directly to EMF electrical energy. It consists of a number of voltaic cells; each voltaic cell consists of two half-cells connected in series by a conductive electrolyte containing anions and cations. One half-cell includes electrolyte and the electrode to which anions (negatively-charged ions) migrate, i.e., the anode or negative electrode; the other half-cell includes electrolyte and the electrode to which cations (positively-charged ions) migrate, i.e., the cathode or positive electrode. In the redox reaction that powers the battery, reduction (addition of electrons) occurs to cations at the cathode, while oxidation (removal of electrons) occurs to anions at the anode. The electrodes do not touch each other but are electrically connected by the electrolyte. Many cells use two half-cells with different electrolytes. In that case each half-cell is enclosed in a container, and a separator that is porous to ions but not the bulk of the electrolytes prevents mixing.

Each half-cell has an electromotive force (or EMF), determined by its ability to drive electric current from the interior to the exterior of the cell. The net EMF of the cell is the difference between the EMFs of it half-cells, as first recognized by Volta. Therefore, if the electrodes have EMFs $\varepsilon 1$ and $\varepsilon 2$, then the net EMF is $\varepsilon 2-\varepsilon 1$; in other words, the net EMF is the difference between the reduction potentials of the half-reactions. The electrical driving force, or $\Delta Vbat$, across the terminals of a cell is known as the terminal voltage (difference), and is measured in volts. The terminal voltage of a cell that is neither charging nor discharging is called the open-circuit voltage, and equals the EMF of the cell. Because of internal resistance, the terminal voltage of a cell that is discharging is smaller in magnitude than the open-circuit voltage, and the terminal voltage of a cell that is charging exceeds the open-circuit voltage. An ideal cell has negligible internal resistance, so it would maintain a constant terminal voltage of $\varepsilon$ until exhausted, then dropping to zero. If such a cell maintained 1.5 volts and stored a charge of one Coulomb, then on complete discharge it would perform 1.5 Joule of work. In actual cells, the internal resistance increases under discharge, and the open circuit voltage also decreases under discharge. If the voltage and resistance are plotted against time, the resulting graphs typically are a curve; the shape of the curve varies according to the chemistry and internal arrangement employed.

As stated above, the voltage developed across a cell's terminals depends on the energy release of the chemical reactions of its electrodes and electrolyte. Alkaline and carbon-zinc cells have different chemistries but approximately the same EMF of 1.5 volts; likewise NiCad and NiMH cells have different chemistries, but approximately the same EMF of 1.2 volts. On the other hand, the high electrochemical potential changes in the reactions of lithium compounds give lithium cells EMFs of 3 volts or more.

Figure 5:
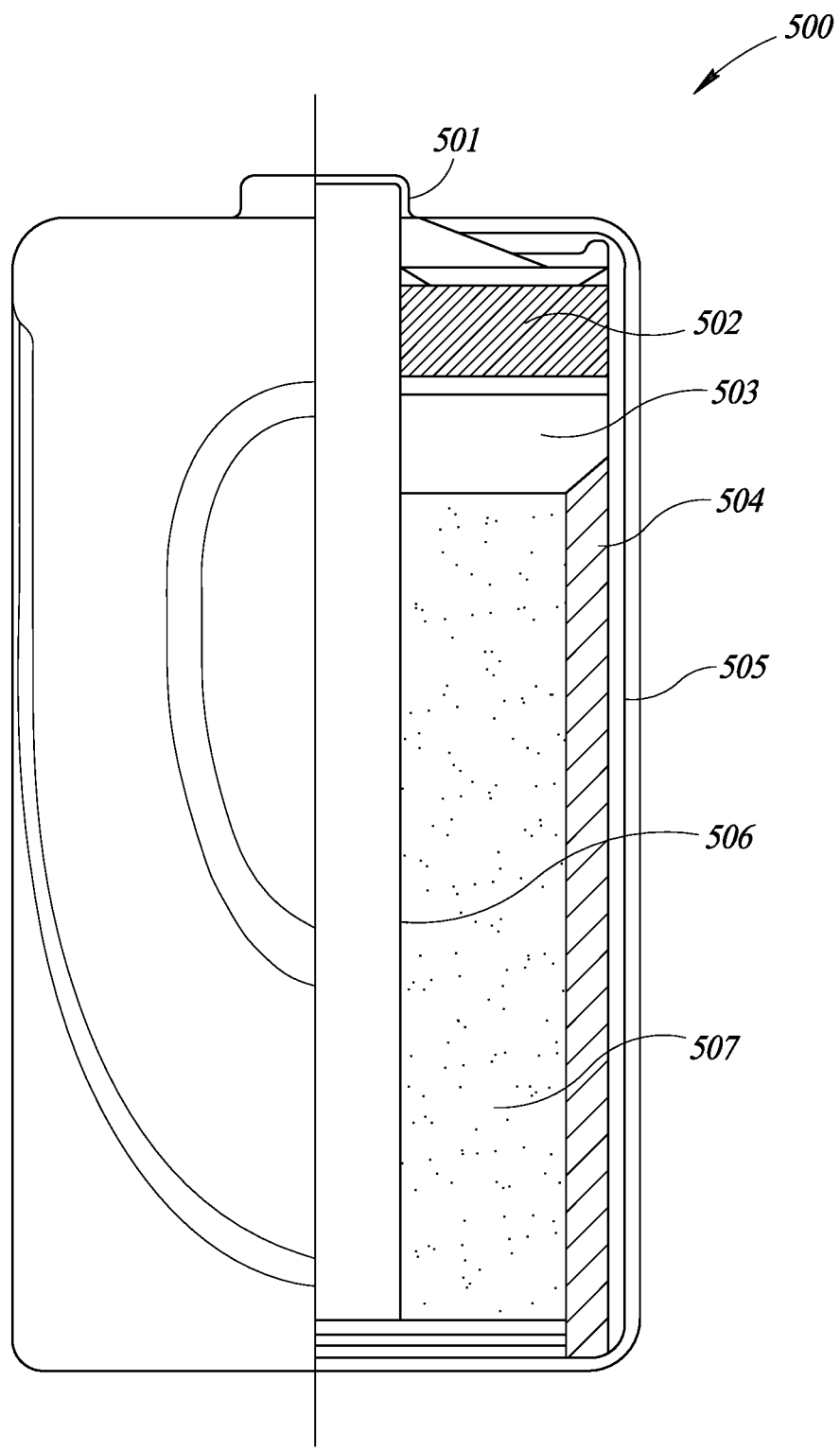
FIG. 5 is a cross-sectional view of a battery that illustrates a battery half-cell, a battery cell, an anode and a cathode.

FIG. 5 shows a conventional battery 500 in cross-section.

The battery may, for example, take the form of a 1.5 VDC EMF primary battery ("D" cell). Components of the battery include:

501. Brass cap—anode connection
502. Plastic seal
503. Expansion space
504. Porous cardboard
505. Zinc surround—cathode and connection
506. Carbon rod—anode
507. Chemical mixture—electrolytic The zinc can (505) forms the negative cathode, the carbon rod (506) forms the positive anode, and the chemical mixture (507) forms the electrolytic. The electrons follow from the negative cathode through an external circuit, performing work, and return to the positive anode to complete the electrons flow circuit.

The Role of Electricity in Evolutionary Biology

Scientists believe that all primitive animals with backbones, including the early ancestors of humans, could sense electricity. As they evolved, mammals, reptiles, birds and most fish lost the ability. Today, only sharks and a few other marine species, such as sturgeons and lampreys, can sense electricity. "Our fishy ancestors had the anatomy for it," said James Albert, a biologist from the University of Louisiana. The ability to sense electrical signals is useful in aquatic environments because water is so conductive. On land, however, the sense is thought useless until the introduction of electric modalities to skin care, via the device described herein.

Skin Compatible Formulation

Method 1

In the "Poke with patch approach" a microneedle device including rollers or patches is placed on the skin to produce pores. The electrochemical formulations including beneficial compounds as desired are rubbed onto the skin thereafter. The formulation penetrates the skin and a tingling will result, due to the EMF, that also should have the healing benefits and potential deeper penetration due to iontophoretic effects.

Method 2

In the "Coat and poke approach" a stable formulation is developed that is used to coat premade microneedle arrays. The array is then placed on the skin and penetrates, allowing drug dissolution and beneficial compound to cross the stratum corneum.

Method 3

For the "Biodegradable microneedles" approach a dissolving microneedle formulation is produced that encapsulates the electric formulation and the beneficial compounds as desired. The needles dissolve under the skin, resulting in the E field generation, tingling and delivery of the beneficial compound.

Method 4

For the "Hollow microneedles" approach a liquid or re-hydratable formulation is vialed that contains the E-formulation and beneficial compounds as desired. The formulation is pulled into a delivery device such as a syringe and then delivered across the stratum corneum through the pores of the hollow microneedle. This approach likely could be rapidly developed and deployed in spas and cosmetic clinics.

Method 5

For the "dip and scrape" approach a beneficial formulation containing the electromotive components is either placed on the skin first or on the microneedle array. The array is rolled or pressed onto the skin after having the beneficial formulation placed on it, and thereby "pushes" the beneficial formulation across the stratum corneum.

Figure 6:
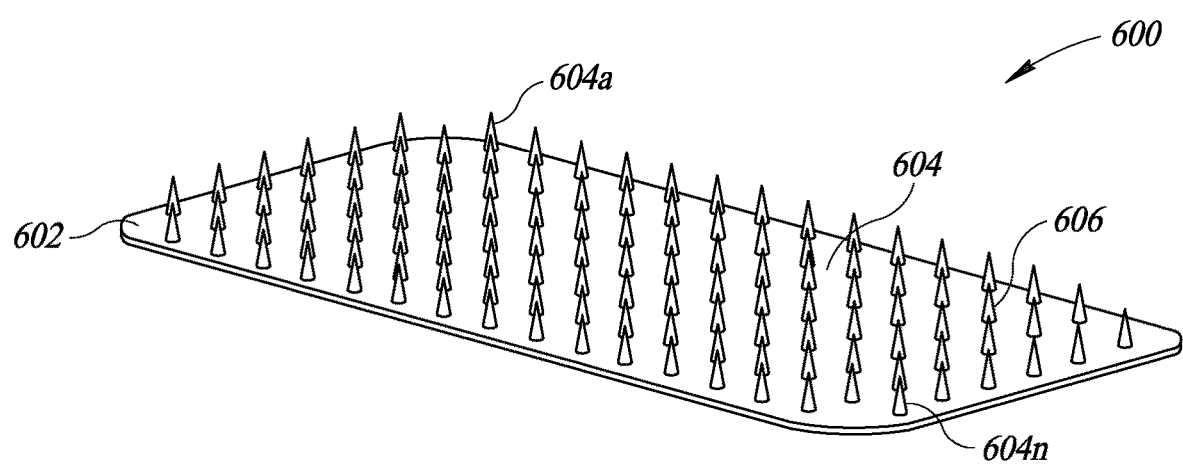
FIG. 6 is an isometric view of a substrate with a plurality of microneedles in an array of microneedles, the microneedles having an electroactive coating or material, according to at least one illustrated embodiment.

FIG. 6 illustrates a coat and poke methodology, according to one illustrated embodiment. A device in the form of a microneedle array patch 600 includes a substrate 602 which has formed thereon or otherwise carries a microneedle array 604 of microneedles 604a-604n (only two called out). An eGel 606 is dried or formulated onto the microneedle array during manufacture and prior to packaging or application to the skin. The coat and poke methodology is the preferred method for fabricating the devices described herein.

The microneedle array patch 600 is fabricated using either carboxymethyl cellulose (CMC or cellulose gum is a cellulose derivative with carboxymethyl groups (—CH2-COOH) bound to some of the hydroxyl groups of the glucopyranose monomers that make up the cellulose backbone) Polyvinylpyrrolidone (PVP, also commonly called polyvidone or povidone, is a water-soluble polymer made from the monomer N-vinylpyrrolidone) or chitosan (a linear polysaccharide composed of randomly distributed (β-(1-4)-linked D-glucosamine (deacetylated unit) and N-acetyl-D-glucosamine (acetylated unit). It is made by treating shrimp and other crustacean shells with the alkali sodium hydroxide.) Referencing FIG. 4, microneedle fabrication, the individual needles 604a-604n are dosed either as discrete battery elements (single microneedle comprised of both anode and cathode) or combinations of battery elements (one microneedle is an anode and another microneedle is a cathode with an electrical path made through the patch).

elSkin Coacervate Synopsis

A coacervate is a tiny spherical droplet of assorted organic molecules (specifically, lipid molecules) which is held together by hydrophobic forces from a surrounding liquid.

Coacervates measure 1 to 100 micrometers across, possess osmotic properties and form spontaneously from certain dilute organic solutions. Their name derives from the Latin coacervare, meaning "to assemble together or cluster". They were once suggested to have played a significant role in the evolution of cells and, therefore, of life itself, and are part of many modern theories of abiogenesis.

Coacervation is a term borrowed from colloid chemistry to describe the basic process of capsule wall formation. The encapsulation process was discovered and developed by Barrett Green of the National Cash Register Corporation (NCR) in the 1940s and 1950s. Actually, coacervative encapsulation (or microencapsulation) is a three-part process: particle or droplet formation; coacervative wall formation; and, capsule isolation. Each step involves a distinct technology in the area of physical chemistry. The first coacervative capsules were made using gelatin as a wall in an "oil-in-water" system. Later developments produced "water-in-oil" systems for highly polar and water soluble cores.

The basic process for using one form of coacervation, also known as aqueous phase separation, was described in an early patent by Green and Schleicher. The patent relates to oil-containing microcapsules of a complex hydrophilic colloid wall material and a method of making them. Green's attempts began in a Dayton, Ohio laboratory. In the late 1930s, Green, a young chemist just out of school, was intrigued by the dearth of information in the colloid field of liquids dispersed in solids. He had earlier recognized the usefulness of such disperse systems in photographic applications. When his company needed a product that would give multiple paper copies without carbon paper, Green turned to his ideas on dispersions. By 1940, the first working No-Carbon-Required (NCR) paper was prepared, but this was only the beginning. His breakthrough came in 1942 when he was investigating Bungenberg de Jong's coacervation studies. One paper mentioned the preparation of solid gelatin spheres, while another dealt with the inclusion of an oil phase within a gelatin coacervate. Green used both concepts and prepared the first gelatin microcapsules. From this beginning it was nine years to the development of a marketable product. The new printing system was triggered by including a colorless dye-base in the oil droplets (coated back, CB) and coating the second sheet of paper (coated front, CF) with acidic clay that could react with the dye-base to produce a color.

Coacervation and Microencapsulation

Coacervation is a colloid phenomenon. If one starts with a solution of a colloid in an appropriate solvent, then according to the nature of the colloid, various changes can bring about a reduction of the solubility of the colloid. As a result of this reduction a large part of the colloid can be separated out into a new phase. The original one-phase system becomes two phases. One is rich and the other is poor in colloid concentration. The colloid-rich phase in a dispersed state appears as amorphous liquid droplets called coacervate droplets. Upon standing, the coacervate droplets coalesce into one clear homogenous colloid-rich liquid layer, known as the coacervate layer, which can be deposited so as to produce the wall material of the resultant capsules.

Coacervation may be initiated in a number of different ways. Examples are changing the temperature, changing the pH or adding a second substance such as a concentrated aqueous ionic salt solution or a non-solvent.

As the coacervate forms, it must wet the suspended core particles or core droplets and coalesce into a continuous coating, for the process of microencapsulation to occur. The final step for microencapsulation is the hardening of the coacervate wall and the isolation of the microcapsules, usually the most difficult step in the total process.

Dextrins are a group of low-molecular-weight carbohydrates produced by the hydrolysis of starch or glycogen. Dextrins are mixtures of polymers of D-glucose units linked by $\alpha$-(1→4) or $\alpha$-(1→6) glycosidic bonds.

Dextrins can be produced from starch using enzymes like amylases, as during digestion in the human body and during malting and mashing, or by applying dry heat under acidic conditions (pyrolysis or roasting). The latter process is used industrially, and also occurs on the surface of bread during the baking process, contributing to flavor, color, and crispness. Dextrins produced by heat are also known as pyrodextrins. During roasting under acid condition the starch hydrolyses and short chained starch parts partially rebranch with $\alpha$-(1,6) bonds to the degraded starch molecule.

Dextrins are white, yellow, or brown powders that are partially or fully water-soluble, yielding optically active solutions of low viscosity. Most can be detected with iodine solution, giving a red coloration; one distinguishes erythrodextrin (dextrin of that color red) and achrodextrin (giving no color).

The immiscible (not forming a homogeneous mixture when added together) chemical phases are:
1. a liquid manufacturing vehicle phase,
2. a core material phase, and
3. a coating material phase.

To form the three phases, the core material is dispersed in a solution of the coating polymer, the solvent for the polymer being the liquid manufacturing vehicle phase. The coating material phase, an immiscible polymer in a liquid state, is formed by utilizing one of the methods of phase separation coacervation, in this procedure by changing the temperature of the polymer solution.

Coacervate Precursor Fabrication

| Ingredient | Scaling % | Procedure |
|---|---|---|
| Anode, cathode or electrolytic payload | | AR |
| Deionized water | 91.00 | |
| Corn Maltodextrin M100 Maltrin | 9.00 | Dry blend into wet |

Figure 7:
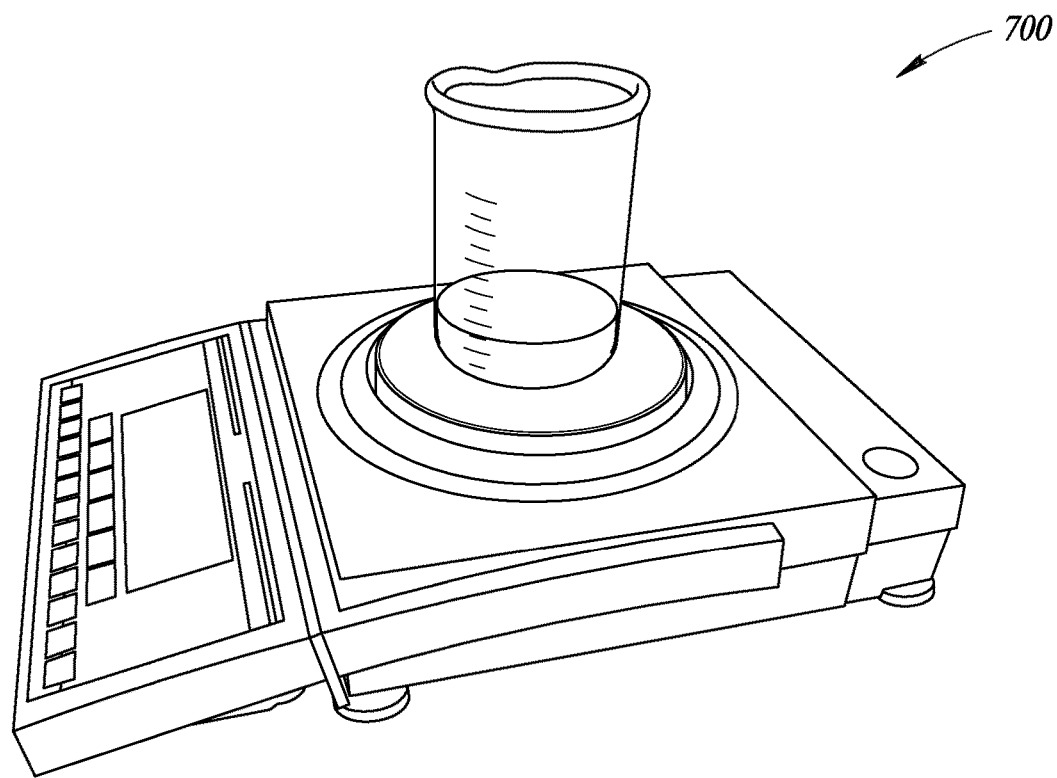
FIG. 7 is a diagram of an electroactive coating or material being applied to microneedles prior to use, according to at least one illustrated embodiment.

FIG. 7 shows a Coacervate Precursor 700, according to one illustrated embodiment.

Figure 8:
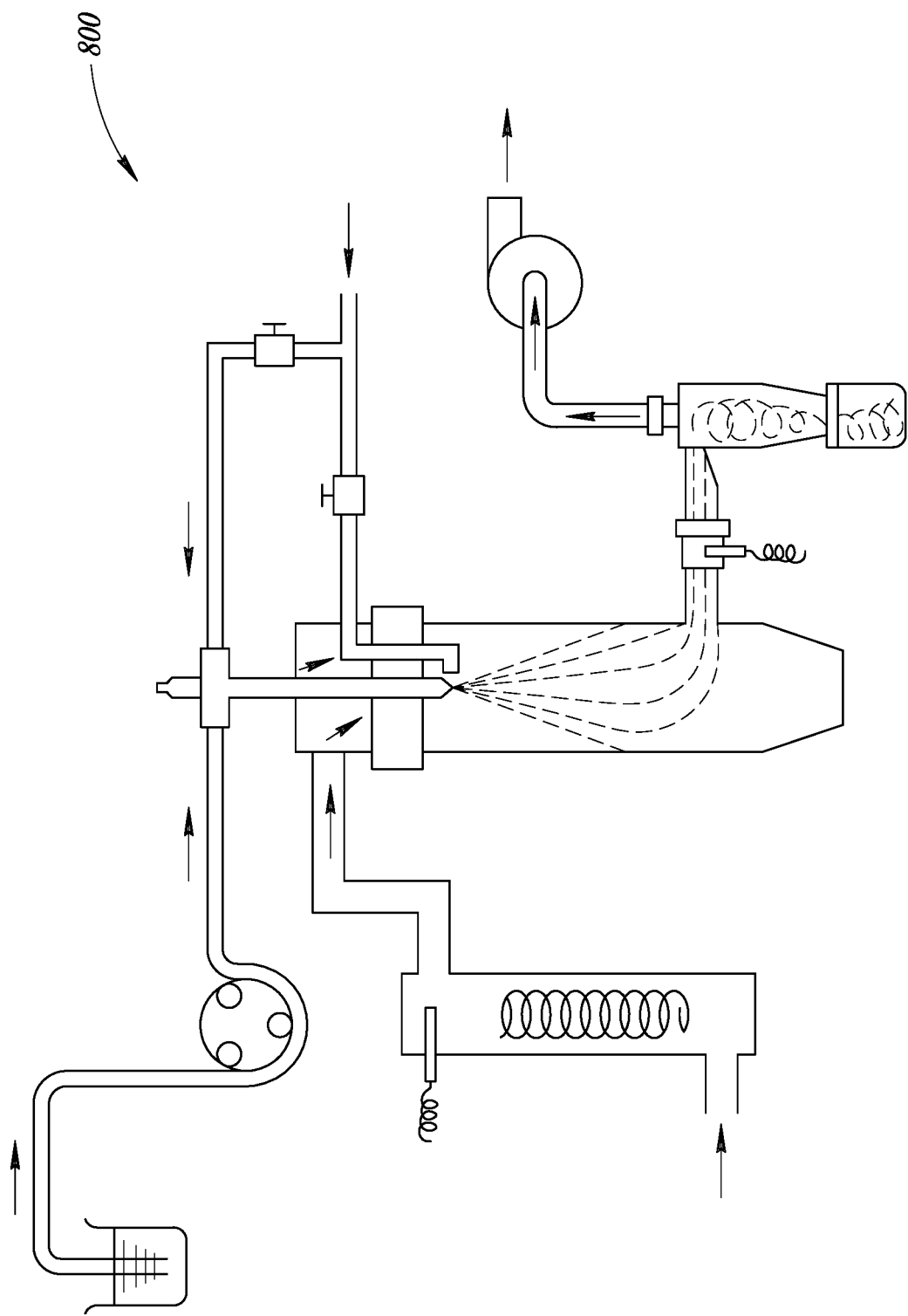
FIG. 8 is a schematic diagram of a system that includes a spray dryer to apply an electroactive coating or material to microneedles, for example, during manufacture of the device and prior to packaging or distribution, according to at least one illustrated embodiment.

FIG. 8 shows a system 800 to fabricate a device, which employs a spray dryer, according to one illustrated embodiment.

The coacervate precursor is sent from a receptacle to the spray nozzle 2 by the fluid pump 1. Clean pressurized air from the compressor is controlled by a needle valve 3 and is sent to the spray nozzle and mixed with the sample at the tip of the nozzle. Then spraying of the sample takes place in the drying chamber 7. At this time, the sample becomes a liquid drop of ~20 um diameter and its surface area will be 3,000 $cm^2$ per 1 ml sample.

Air will be sucked into the equipment by the aspirator 10 and it will be heated to the set temperature by the heater 5. This hot air is sucked into the drying chamber to contact with the sprayed sample drop, and dries the sample instantaneously. Since the contact area of the sample and hot air is very large, more than 90% of the moisture will be vaporized by the hot air instantly in the drying chamber.

The dried sample, in fine particle, is dried further and will be sent to the cyclone 8, then separated from all vapor, and will be collected in the product vessel 9. It usually takes 0.5 seconds or less. Since the sample particle is always surrounded by vaporized solvent (steam), the temperature around each fine particle will not be raised much by the heat of vaporization. Heat sensitive materials, such as enzymes, can be powdered with little loss of activity at relatively high temperature (80 degree C.).

The steam and air mixture will exhaust outside through the aspirator.

The temperature condition of test operation will be shown on the display panel by detecting the inlet and outlet temperature through each sensor.

If adhesion of the sample to the tip of the nozzle becomes serious, compressed air is blown against the tip of the nozzle from the distributor 6 by opening the electromagnetic valve 4 to remove these adhesives. Air, if necessary, can be introduced into the chamber by removing the cap 11.

Once the coacervate precursor is formulated, the microneedle array can be selectivity coated either in a discrete modality (anode and cathode) or multiple array (requires electrical connection back through the patch).

Microneedle Usage

When oral administration of drugs is not feasible due to poor drug absorption or enzymatic degradation in the gastrointestinal tract or liver, injection using a painful hypodermic needle is the most common alternative. An approach that is more appealing to patients, and offers the possibility of controlled release over time, is drug delivery across the skin using a patch. However, transdermal delivery is severely limited by the inability of the large majority of drugs to cross skin at therapeutic rates due to the great barrier imposed by skin's outer stratum corneum layer. To increase skin permeability, a number of different approaches have been studied, ranging from chemical/lipid enhancers to electric fields employing iontophoresis and electroporation to pressure waves generated by ultrasound or photo-acoustic effects. Although the mechanisms are all different, these methods share the common goal to disrupt stratum corneum structure in order to create "holes" large enough for molecules to pass through. The size of disruptions generated by each of these methods is believed to be of nanometer dimensions, which are large enough to permit transport of small drugs and, in some cases, macromolecules, but probably small enough to prevent causing damage of clinical significance.

An alternative approach involves creating larger transport pathways of microns dimensions using arrays of microscopic needles. These pathways are orders of magnitude bigger than molecular dimensions and, therefore, should readily permit transport of macromolecules, as well as possibly supramolecular complexes and micro-particles. Despite their very large size relative to drug dimensions, on a clinical length scale they remain small. Although safety studies need to be performed, it is proposed that micronscale holes in the skin are likely to be safe, given that they are smaller than holes made by hypodermic needles or minor skin abrasions encountered in daily life. Transdermal drug delivery is a noninvasive, user-friendly delivery method for therapeutics. However, its clinical use has found limited application due to the remarkable barrier properties of the outermost layer of skin, the stratum corneum (SC). Physical and chemical methods have been developed to overcome this barrier and enhance the transdermal delivery of drugs. One of such techniques was the use of microneedles to temporarily compromise the skin barrier layer. This method combines the advantages of conventional injection needles and transdermal patches while minimizing their disadvantages. As compared to hypodermic needle injection, microneedles can provide a minimally invasive means of painless delivery of therapeutic molecules through the skin barrier with precision and convenience.

The microneedles seldom cause infection while they can allow drugs or nanoparticles to permeate through the skin. Increased microneedle-assisted transdermal delivery has been demonstrated for a variety of compounds. For instance, the flux of small compounds like calcein, diclofenac methyl nicotinate was increased by microneedle arrays. In addition, microneedles also have been tested to increase the flux of permeation for large compounds like fluorescein isothiocynate-labeled Dextran, bovine serum albumin, insulin and plasmid DNA and nano-spheres.

Mechanism of Action

Figure 9:
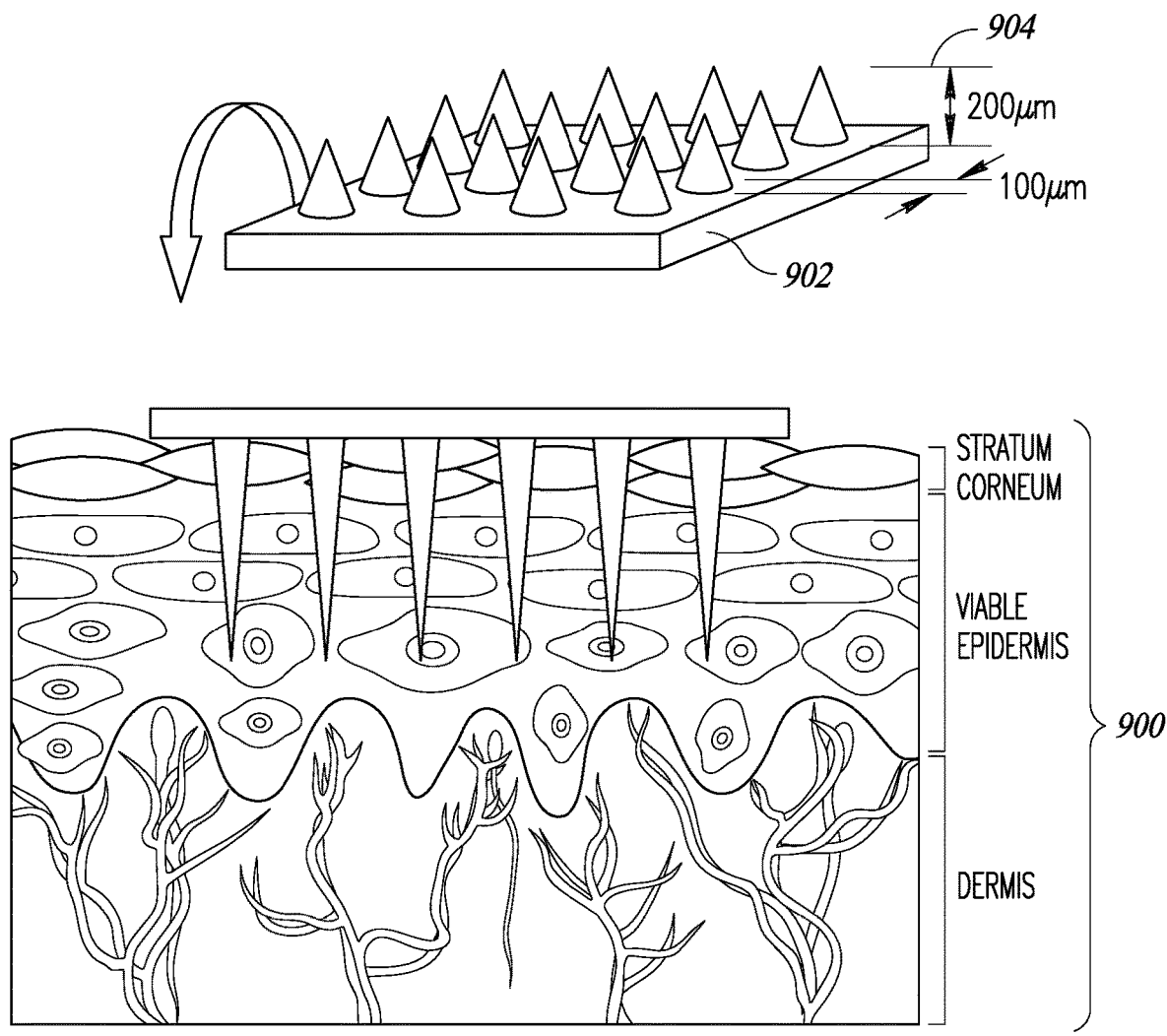
FIG. 9 is a cross-sectional diagram of a bodily interface tissue in the form of skin, with a device comprising an array of microneedles positioned to pierce or abrade a layer of the skin and provide an electromotive force thereto, according to at least one illustrated embodiment.

With reference to FIG. 9, the mechanism for delivery is not based on diffusion as it is in other transdermal drug delivery products. Instead, it is based on the temporary mechanical disruption of the skin 900 and the placement of the drug or vaccine within the epidermis, where it can more readily reach its site of action. The drug, in the form of biomolecules, is encapsulated on or within the microneedles 904 carried or form on or in a substrate 902, which are then inserted into the skin 900 in the same way a drug like nitroglycerine is released into the bloodstream from a patch. The cargo and or microneedles 904 dissolve within minutes, releasing the trapped cargo at the intended delivery site. The microneedles 904 do not need to be removed and no dangerous or biohazardous substance is left behind on the skin 900, as the microneedles 904 are made of a biodegradable substance. In microneedle devices, a small area (the size of a traditional transdermal patch) is covered by tens to hundreds of microneedles 904 formed in a matrix that penetrate (pierce) only the stratum corneum (the uppermost 50 μm of the skin 900), thus allowing the drug to bypass this important barrier.

The tiny microneedles 904 are constructed in arrays to deliver sufficient amount of drug to the patient for the desired therapeutic response.

Preparation of Microneedles

Molding

Figure 10:
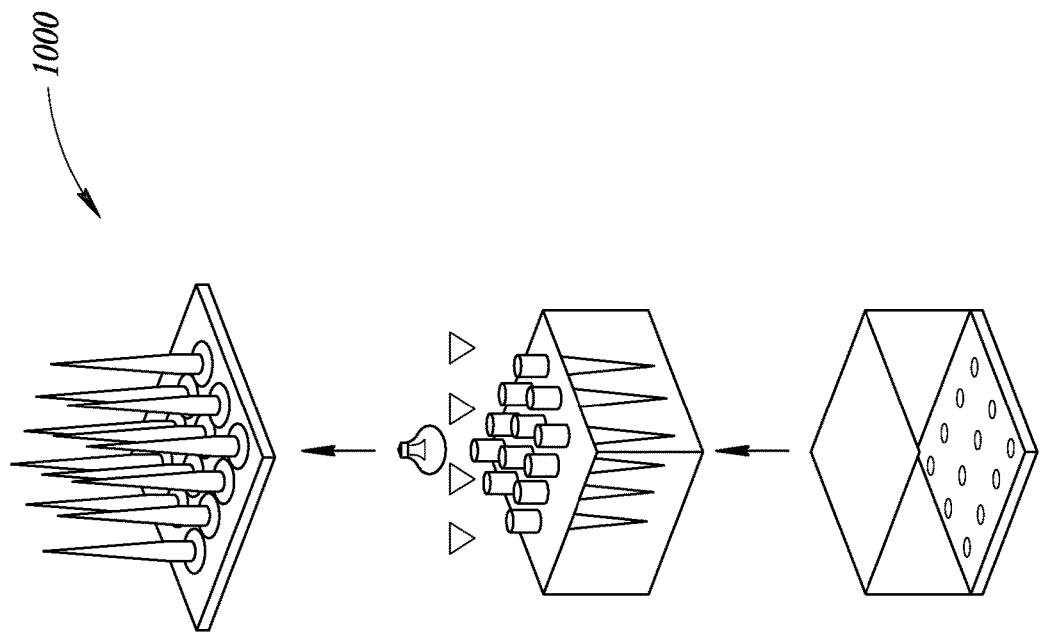
FIG. 10 is a schematic diagram of a method of manufacturing micromolds to fabricate microneedles with electrical potential properties, according to at least one illustrated embodiment.
Figure 10:
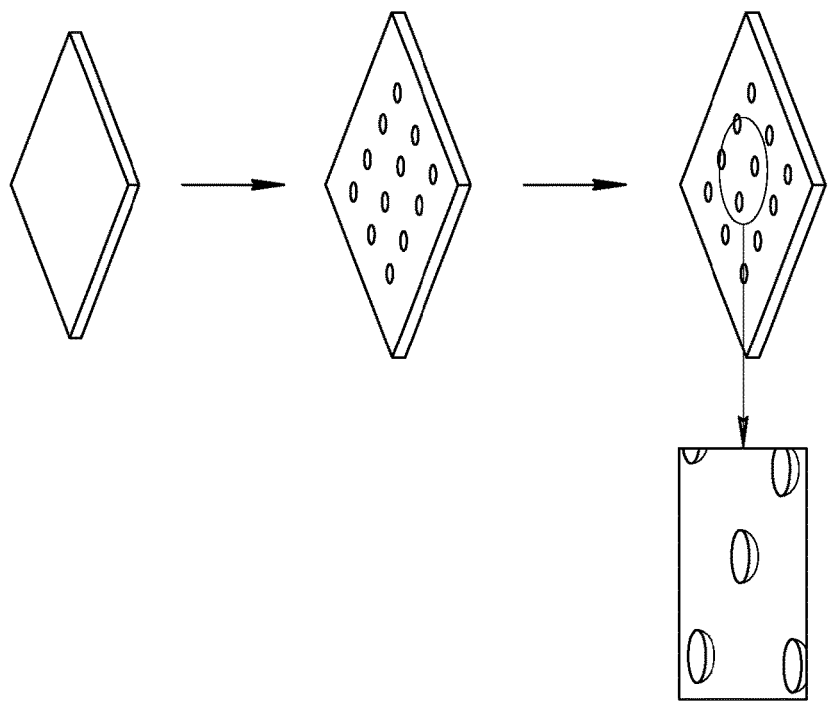
Figure 11:
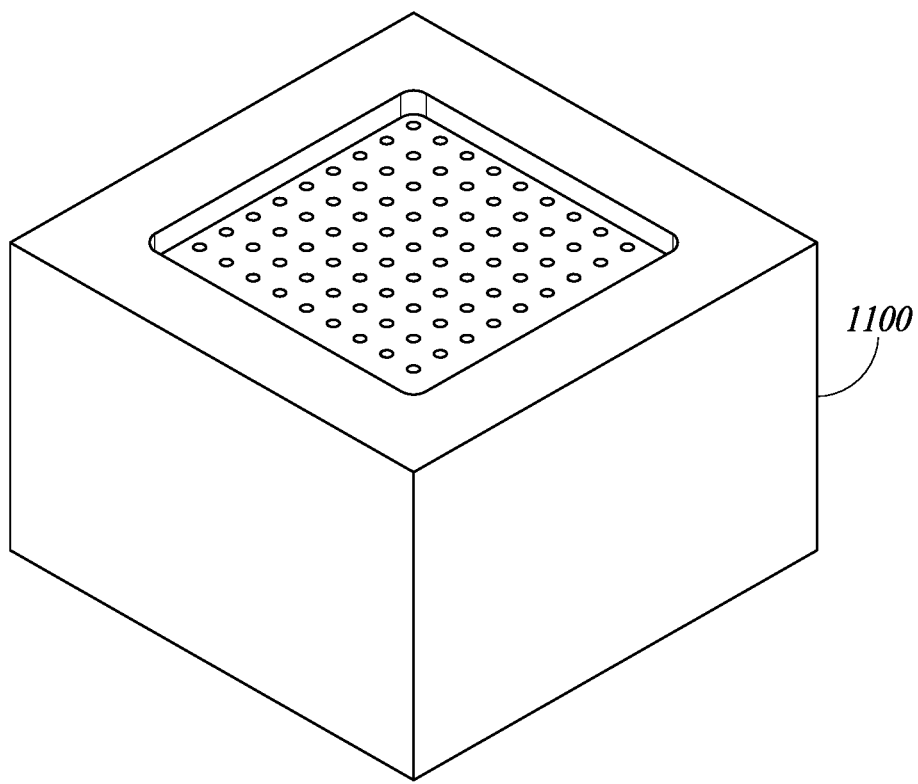
FIG. 11 is an isometric view of a casting created during the method of FIG. 10, according to at least one illustrated embodiment.

As illustrated in FIG. 10, micromolds are fabricated using photolithography and a molding process 1000. In brief, a female microneedle master-mold was structured in SU-8 photoresist (SU-8 is a commonly used epoxy-based negative photoresist. Negative refers to a photoresist whereby the parts exposed to UV become cross-linked, while the remainder of the film remains soluble and can be washed away during development) by UV exposure to create conical (circular cross section) or pyramidal (square cross section) microneedles tapering from a base measuring 300 μm to a tip measuring 25 μm in width over a microneedle length of 600-800 μm, 700 μm nominal. As illustrated in FIG. 11, a male microneedle master-structure 1100 made of polydimethylsiloxane was created using this mold. The PDMS master-structure was sputter coated (Cressington 108) with 100 nm of gold to prevent adhesion with a second PDMS layer cured onto the male master-structure to create a female PDMS replicate-mold (reference FIG. 2a). Excess PDMS on the female replicate-mold was trimmed so that the mold fit within the 27 mm inner diameter of a 50 ml conical tube. This metal coated male master-structure was repeatedly used to make replicate-molds that were repeatedly used to make microneedle units.

Preparation of the Microneedle Matrix

To serve as microneedle matrix materials, ultra-low viscosity carboxymethylcellulose (CMC), amylopectin and bovine serum albumin (BSA) were dissolved in deionized water. Water was then evaporated off until the concentration of solute (e.g., CMC) was approximately 27 weight %, which resulted in a viscous hydrogel. CMC was concentrated by heating at 60-70° C. at ambient pressure or vacuuming at −50 kPa at room temperature. Amylopectin and BSA were concentrated only by the heating method at 60 to 70° C. or 37° C., respectively. Solute concentration was determined by measuring solution mass before and after evaporation. Viscosity of concentrated hydrogels was measured using a Couette viscometer. In some cases, a model (test) drug was added by hand mixing to solubilize or suspend the compound in the concentrated hydrogel. Three model (test) drugs were added at final concentrations of 0.15-30 weight % sulforhodamine B (Molecular Probes), 20 weight % BSA (Sigma), or 5 weight % lysozyme (Sigma). The term "model drug" is used to indicate that these compounds have physicochemical and transport properties representative of a certain classes of drugs, but not to suggest that these compounds have pharmacological activity representative of drugs.

When employing a hydrogel (solubilize with the payloads) for the microneedle base, rather than a chitin (exterior microneedle coating), the drug (e.g., hyaluronic acid typically) and organoleptic (anode/cathode pair typically Cu and Zn) are sacrificial and will partially to fully dissolve in the stratum corneum.

Casting of the Microneedle Matrix

To mold microneedles from concentrated hydrogels, 100-300 mg of hydrogel was placed on a female PDMS mold in a conical centrifuge tube (Corning) and centrifuged (Sorvall Legend RT) in a 45° angled rotor at 3000 RPM and 37° C. for up to 2 hour to fill the microneedle mold cavities and dry the hydrogel.

To prepare microneedles with the model drug and/or organoleptic (cathode and anode) encapsulated only within the microneedles and not in the backing layer, 8-10 mg of hydrogel mixed with model drug or organoleptic was filled just into the microneedle cavities in the mold and then dried under centrifugation for up to 30 minutes. Residual hydrogel on the surface of the mold was removed with dry tissue paper and 100-200 mg pure hydrogel without drug was then applied and dried onto the mold to form the backing layer.

Optionally—to prepare microneedles with model drug and/or organoleptic encapsulated only in the backing layer and not within the microneedles, the same two-step process was followed, except pure hydrogel was filled into the microneedle mold cavities and a hydrogel mixed with model drug was used to form the backing layer.

Figure 12A:
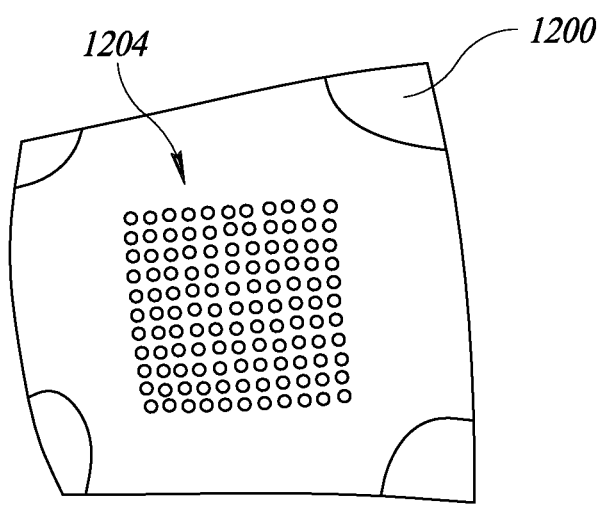
FIG. 12A is an isometric view of a device comprising a substrate with a plurality of microneedles with electrical potential properties in an ordered array, according to at least one illustrated embodiment.
Figure 12B:
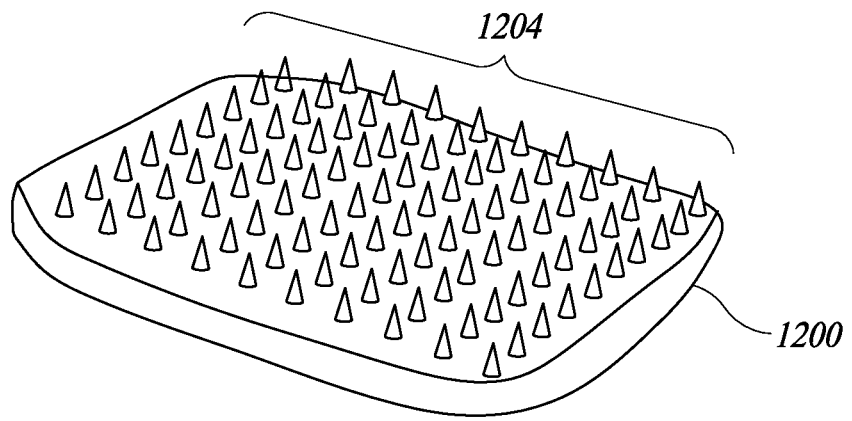
FIG. 12B is another isometric view of the device of FIG. 12A.

FIGS. 12A and 12B illustrate the resulting structure 1200 which includes a plurality of microneedles 1204.

Figure 13:
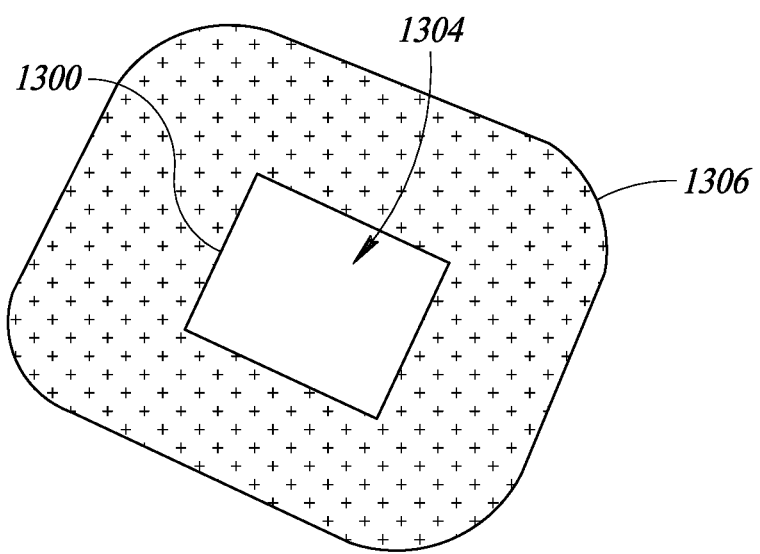
FIG. 13 is an isometric view of a device comprising a substrate with a plurality of microneedles with electrical potential properties in an ordered array and an adhesive backing, according to at least one illustrated embodiment.

FIG. 13 shows a structure 1300 which includes a plurality of microneedles 1304 and an adhesive backing 1306 to allow the structure 1300 to be removably secured to tissue (e.g., skin). The adhesive backing 1306 may include or comprise a pressure-sensitive adhesive, which is preferably bio-compatible. A release liner may overlie the pressure-sensitive adhesive, and is removed just prior to use to expose the pressure-sensitive adhesive.

Active Drug (One of Several Available)

Hyaluronan (also called hyaluronic acid) is an anionic, nonsulfated glycosaminoglycan distributed widely throughout connective, epithelial, and neural tissues. It is unique among glycosaminoglycans in that it is nonsulfated, forms in the plasma membrane instead of the Golgi, and can be very large, with its molecular weight often reaching the millions. One of the chief components of the extracellular matrix, hyaluronan contributes significantly to cell proliferation and migration. The average 70 kg (154 lb.) person has roughly 15 grams of hyaluronan in the body, one-third of which is turned over (degraded and synthesized) every day.

Hyaluronic acid is derived from hyalos (Greek for vitreous) and uronic acid because it was first isolated from the vitreous humour and possesses a high uronic acid content. The term hyaluronate refers to the conjugate base of hyaluronic acid. Because the molecule typically exists in vivo in its polyanionic form, it is most commonly referred to as hyaluronan.

Until the late 1970s, hyaluronan was described as a "goo" molecule, a ubiquitous carbohydrate polymer that is part of the extracellular matrix. For example, hyaluronan is a major component of the synovial fluid, and was found to increase the viscosity of the fluid. Along with lubricin, it is one of the fluid's main lubricating components.

Hyaluronan is an important component of articular cartilage, where it is present as a coat around each cell (chondrocyte). When aggrecan monomers bind to hyaluronan in the presence of HAPLN1 (Hyaluronan and proteoglycan link protein 1), large, highly negatively charged aggregates form. These aggregates imbibe water and are responsible for the resilience of cartilage (its resistance to compression). The molecular weight (size) of hyaluronan in cartilage decreases with age, but the amount increases.

Hyaluronan is also a major component of skin, where it is involved in tissue repair. When skin is exposed to excessive UVB rays, it becomes inflamed (sunburn) and the cells in the dermis stop producing as much hyaluronan, and increase the rate of its degradation. Hyaluronan degradation products then accumulate in the skin after UV exposure.

Hyaluronan and Skin Healing

Hyaluronic acid (HA) plays an important role in the normal epidermis. HA also has crucial functions in the reepithelization process due to several of its properties. It serves as an integral part of the extracellular matrix of basal keratinocytes, which are major constituents of the epidermis; its free-radical scavenging function and its role in keratinocyte proliferation and migration.

In normal skin, HA is found in relative high concentrations in the basal layer of the epidermis where proliferating keratinocytes are found. CD44 is collocated with HA in the basal layer of epidermis where additionally it has been shown to be preferentially expressed on plasma membrane facing the HA-rich matrix pouches. Maintaining the extracellular space and providing an open, as well as hydrated, structure for the passage of nutrients are the main functions of HA in epidermis. It has been found HA content increases at the presence of retinoic acid (vitamin A). The proposed effects of retinoic acid against skin photo-damage and aging may be correlated, at least in part, with an increase of skin HA content, giving rise to increase of tissue hydration. It has been suggested the free-radical scavenging property of HA contributes to protection against solar radiation, supporting the role of CD44 acting as a HA receptor in the epidermis.

Epidermal HA also functions as a manipulator in the process of keratinocyte proliferation, which is essential in normal epidermal function, as well as during reepithelization in tissue repair. In the wound healing process, HA is expressed in the wound margin, in the connective tissue matrix, and collocating with CD44 expression in migrating keratinocytes. Kaya et al. found suppression of CD44 expression by an epidermis-specific antisense transgene resulted in animals with defective HA accumulation in the superficial dermis, accompanied by distinct morphologic alterations of basal keratinocytes and defective keratinocyte proliferation in response to mitogen and growth factors. Decrease in skin elasticity, impaired local inflammatory response, and impaired tissue repair were also observed. Their observations are strongly supportive of the important roles HA and CD44 have in skin physiology and tissue repair.

While it is abundant in extracellular matrices, hyaluronan also contributes to tissue hydrodynamics, movement and proliferation of cells, and participates in a number of cell surface receptor interactions, notably those including its primary receptors, CD44 and RHAMM. Upregulation of CD44 itself is widely accepted as a marker of cell activation in lymphocytes. Hyaluronan's contribution to tumor growth may be due to its interaction with CD44. Receptor CD44 participates in cell adhesion interactions required by tumor cells.

Although hyaluronan binds to receptor CD44, there is evidence hyaluronan degradation products transduce their inflammatory signal through toll-like receptor 2 (TLR2), TLR4 or both TLR2, and TLR4 in macrophages and dendritic cells. TLR and hyaluronan play a role in innate immunity. There are limitations including the in vivo loss of this compound limiting the duration of effect.

Galvanic Compatibility

A battery is a device that converts chemical energy directly to EMF electrical energy. The battery comprises a number of voltaic cells; each voltaic cell consists of two half cells connected in series by a conductive electrolyte containing anions and cations. One half-cell includes electrolyte and the electrode to which anions (negatively-charged ions) migrate, i.e., the anode or negative electrode; the other half-cell includes electrolyte and the electrode to which cations (positively-charged ions) migrate, i.e., the cathode or positive electrode. In the redox reaction that powers the battery, reduction (addition of electrons) occurs to cations at the cathode, while oxidation (removal of electrons) occurs to anions at the anode. The electrodes do not touch each other but are electrically connected by the electrolyte. Many cells use two half-cells with different electrolytes. In that case each half-cell is enclosed in a container, and a separator that is porous to ions but not the bulk of the electrolytes prevents mixing.

The galvanic compatibility of two different metals may be predicted by consideration of their "Anodic Index". This parameter is a measure of the electrochemical voltage that will be developed between the metal and gold. To find the relative voltage of a binary of metals it is only required to subtract their Anodic Indexes.

For example in elSkin a common cathodic/anodic pair is employed (FDA GRAS compounds are observed):

Copper and Zinc=(−0.350 V)−(1.250 V)=0.900 Volt or 900 mV

| Anodic index Metal (V) | Index |
|---|---|
| Most Cathodic | |
| Gold, solid and plated, Gold-platinum alloy | 0.000 |
| Rhodium plated on silver-plated copper | −0.050 |
| Silver, solid or plated; monel metal. High nickel-copper alloys | −0.150 |
| Nickel, solid or plated, titanium as alloys, Monel | −0.300 |
| Copper, solid or plated; low brasses or bronzes; silver solder; German silvery high copper-nickel alloys; nickel-chromium alloys | −0.350 |
| Brass and bronzes | −0.400 |
| High brasses and bronzes | −0.450 |
| 18% chromium type corrosion-resistant steels | −0.500 |
| Chromium plated; tin plated; 12% chromium type corrosion-resistant steels | −0.600 |
| Tin-plate; tin-lead solder | −0.650 |
| Lead, solid or plated; high lead alloys | −0.700 |
| 2000 series wrought aluminum | −0.750 |
| Iron, wrought, gray or malleable, plain carbon and low alloy steels | −0.850 |
| Aluminum, wrought alloys, 2000 series aluminum, cast alloys of the silicon type | −0.900 |
| Aluminum, cast alloys other than silicon type, cadmium, plated and chromate | −0.950 |
| Hot-dip-zinc plate; galvanized steel | −1.200 |
| Zinc, wrought; zinc-base die-casting alloys; zinc plated | −1.250 |
| Magnesium & magnesium-base alloys, cast or wrought | −1.750 |
| Beryllium | −1.850 |
| Most Anodic | |

Organoleptic

Scientists believe that all primitive animals with backbones, including the early ancestors of humans, could sense electricity. As they evolved, mammals, reptiles, birds and most fish lost the ability. Today, only sharks and a few other marine species, such as sturgeons and lampreys, can sense electricity. "Our fishy ancestors had the anatomy for it," said James Albert, a biologist from the University of Louisiana. The ability to sense electrical signals is useful in aquatic environments because water is so conductive. On land, however, the sense is thought useless until the introduction of electric modalities to skin care, such as the devices described herein (denominated as elSkin for convenience).

Adjuvant—Integration

Cosmetic electrotherapy is a range of beauty treatments that uses low electric currents passed through the skin to produce several therapeutic effects such as muscle toning in the body and micro-lifting of the face. It is based on electrotherapy, which has been researched and accepted in the field of rehabilitation, though the "scientific and medical communities have tended to side-line or dismiss the use of electrotherapy for healthy muscles."

An adjuvant (from Latin, adiuvare: to aid) is a pharmacological and/or immunological agent that modifies the effect of other agents. By dosing multiple of the microneedles with a drug (for our application of facial treatment Hyaluronic acid (HA)) and other needles with a combination of anodic and cathodic elements an adjuvant is formed, both organoleptic effect ("tingling") and for therapeutic value.

Figure 14:
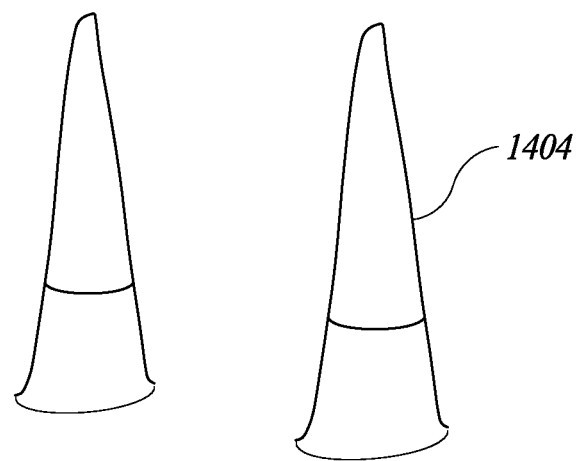
FIG. 14 is a false color enlarged isometric view of a plurality of microneedles with electrical potential properties, showing layering therein, according to at least one illustrated embodiment.

The cathodic/anodic pair microneedles 1404 can be cast in single microneedle stack/layers of cathode (reference FIG. 14), separator and anode or in an alternative configuration one microneedle cast as a cathode and another as an anode, the device's substrate or backing can be form a conductive path and the dermis the other.

Figure 15:
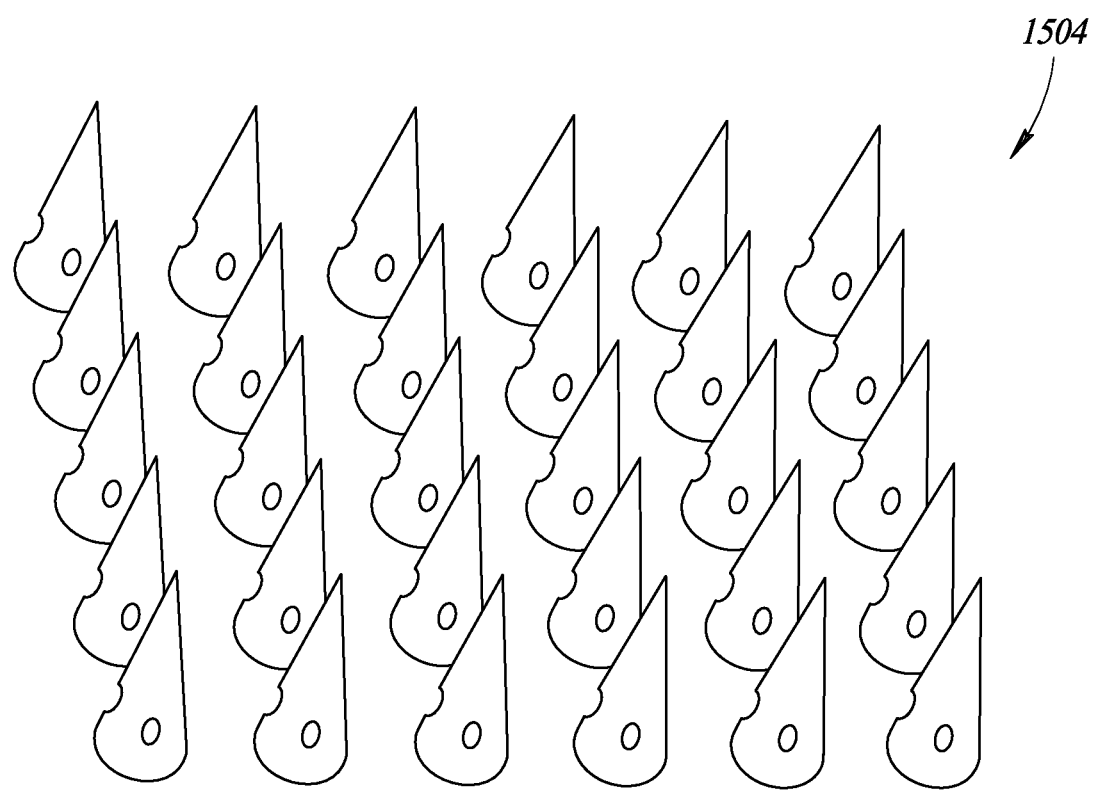
FIG. 15 is a scanning electron microscopic image of a plurality of microneedles with electrical potential properties, according to at least one illustrated embodiment.

FIG. 15 shows an ordered array of microneedles 1504, according to various implementations described herein.

It is possible that the cathodic/anodic can be connected in series and or parallel by the backing layer to form different voltages and resistance modifying the organoleptic effect and therapeutic value.

Geometry

Figure 16:
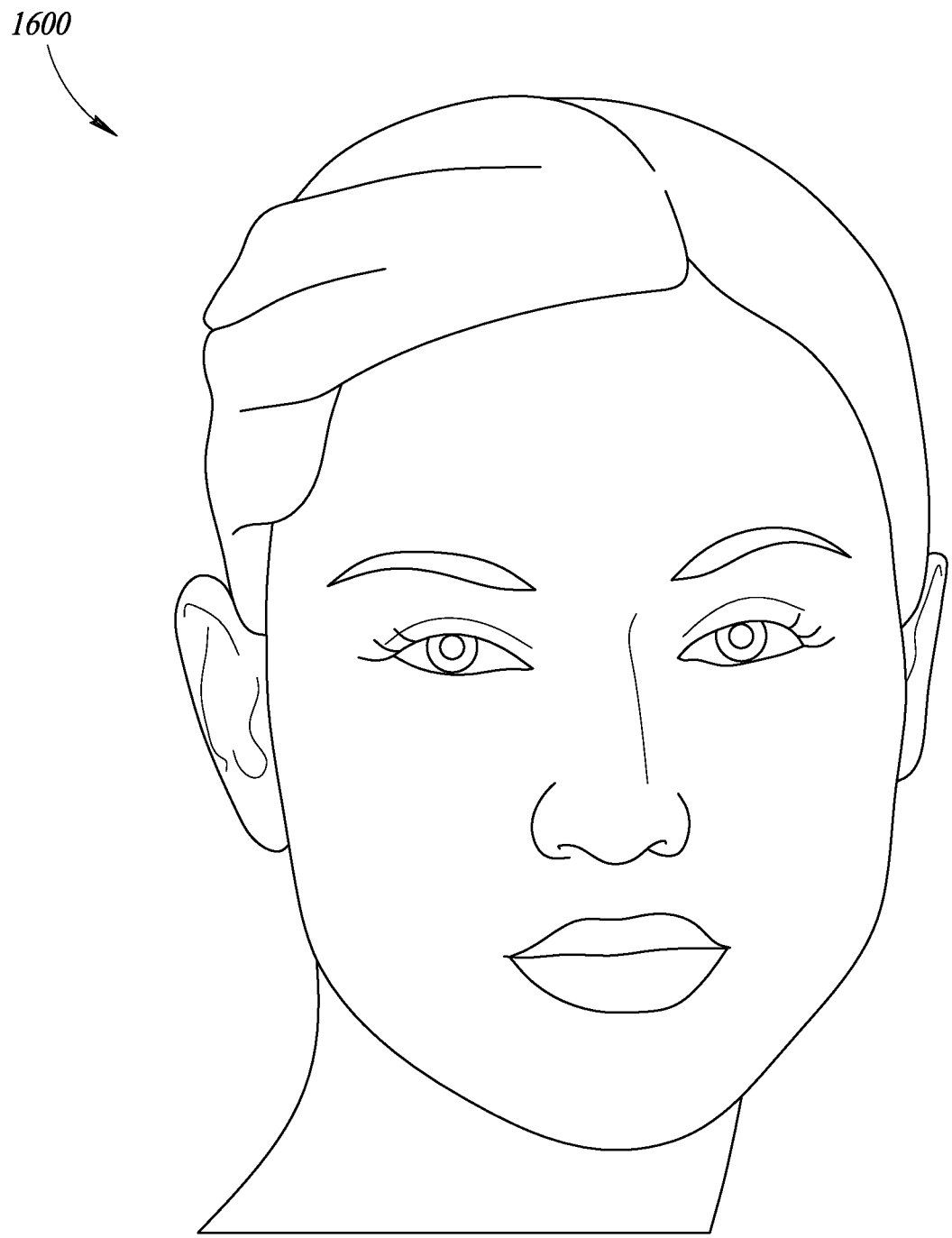
FIG. 16 is an isometric view of a face, on which a device having a plurality of microneedles with electrical potential properties may be advantageously employed, according to at least one illustrated embodiment.

Depending on the skin type (European, Asian, etc.), condition and surface area to be treated, with emphasis on a face 1600 (FIG. 16) different mechanical geometries of functionalized microneedle device (elSkin) can be fabricated:

1. Y axis count
2. X axis count
3. Microneedle format, e.g. conical or pyramidal
4. Microneedle length, μm
5. Microneedle diameter, μm
6. Microneedle pitch (center line to center line), μm
7. Microneedle drug and cathodic/anodic organoleptic
8. Backing dimensions
9. Microneedle material fabrication material (e.g. concentrated hydrogel) and dosing Facial Regions FIG. 16 shows various facial regions of a face 1600, on which the devices described herein may be used, either with or without a cosmetic or pharmaceutical composition.

Microneedle geometry in terms of varying center-to-center spacing has been shown to be a crucial factor in the penetration profile into skin. An increase in force per needle is seen with increased center-to-center spacing of needles for all base diameters, thus suggesting that needles with higher center-to-center spacing are able to penetrate the skin better. This correlates well with findings where an increase in needle interspacing results in lower resistance for penetration in skin, which could result in higher needle penetration rates, and thus, a greater quantity of drug delivery.

Apart from center-to-center spacing, 300 μm and 400 μm base diameter needles showed the most promising penetration profiles with high penetration rates, while 200 μm base diameter needles had a low penetration rate, which could be attributed to its thin needle profile that results in a weaker structure which buckles more easily upon insertion onto the surface of the skin than for needles of larger base diameters. Microneedles with 300 μm base diameter, 1800 μm spacing, and 400 μm base diameters, 2400 μm spacing gave consistent and relatively high percentage of microneedles penetrating the skin. In addition, because sharper needles have a larger length-to-base aspect ratio, needles with a smaller length-to-base aspect ratio penetrate skin better.

Comparative Benefits/Advantages

Higher effectivity

Reduction of time to yield compared to passive strictly chemical-based facial anti-aging products.

Diminish appearance of fine lines and wrinkles

Enhance production of healthy, new radiant skin

Hydrate skin so it's more plump, firm and healthier

Reduce appearance of dark spots and hyperpigmentation

Organoleptic, e.g., tingling sensation

A microchannel based transdermal delivery system thru the usage of microneedles is an innovative approach toward a skin care drug delivery system. It is a convenient, painless, and less invasive alternative to injection (e.g. Botox requiring an office procedure) and it can be used as a common method for effective administering large proteins, peptides, antibiotics, vaccines adjuvant with EMF organoleptic(s) with a low manufacturing cost.

Applications beyond skin care are suggested, e.g. wound and scar tissue management.

Wound Healing

Wound healing is the process by which skin or other body tissue repairs itself after trauma. In undamaged skin, the epidermis (surface layer) and dermis (deeper layer) form a protective barrier against the external environment. When the barrier is broken, an orchestrated cascade of biochemical events is set into motion to repair the damage. This process is divided into predictable phases: blood clotting (homeostasis), inflammation, tissue growth (proliferation) and tissue remodeling (maturation). Blood clotting may be considered to be part of the inflammation stage instead of a separate stage.

Electrical stimulation offers a unique treatment option to heal complicated and recalcitrant wounds, improve flap and graft survival, and even improve surgery results. Electrical stimulation may reduce infection, improve cellular immunity, increase perfusion, and accelerate wound healing. Further, the delivery of anti-microbial compounds can be more effective using electrical stimulation.

Metal ions like copper and zinc ions are standalone antiseptic agents and are able to kill bacteria, both gram positives and gram negatives as well as denature viruses and protein toxins. Drug resistant bacteria like MRSA are also effectively killed by these metal ions.

Producing a nanostructure cell that generates an electric field by the interaction of Cu and Zn can result in both improved healing due to the electric stimulation and antiseptic properties due to the resultant metal ions being produced. A bandage that combines these properties may result in better treatment outcomes and more rapid healing of affected, damaged sites.

Wound healing is classically divided into four phases: hemostasis, inflammation, proliferation, and remodeling. Although a useful construct, this model employs considerable overlapping among individual phases. A complementary model has recently been described where the many elements of wound healing are more clearly delineated. The importance of this new model becomes more apparent through its utility in the fields of regenerative medicine and tissue engineering. In this construct, the process of wound healing is divided into two major phases: 1. the early phase, and 2. the cellular phase.

The early phase, which begins immediately following skin injury, involves cascading molecular and cellular events leading to hemostasis and formation of an early, makeshift extracellular matrix that provides structural staging for cellular attachment and subsequent cellular proliferation.

The cellular phase involves several types of cells working together to mount an inflammatory response, synthesize granulation tissue, and restore the epithelial layer.

Subdivisions of the cellular phase are:

1. Macrophages and inflammatory components, within 1-2 days,

2. Epithelial-mesenchymal interaction: re-epithelialization, phenotype change within hours, migration begins on day 1 or 2, 3. Fibroblasts and myofibroblasts: progressive alignment, collagen production, and matrix contraction, between day 4 day 14, 4. Endothelial cells and angiogenesis, begins on day 4, and 5. Dermal matrix: elements of fabrication, begins on day 4, lasting 2 weeks and alteration/remodeling, begins after week 2, lasting weeks to months—depending on wound size.

Electric Fields for Wound Healing

The human cell is an electrical unit. The initial measurements of the transcutaneous voltage across the human skin by Baker et al. were later validated through a larger study of 17 health volunteers. More recent investigation has shown that all living cells are enveloped by a plasma membrane that operates on the electrochemical physiology principle of DC exchange of ions. Injury to the epithelial layer disrupts the body's naturally occurring electrical current therefore creating an electrical field. This electrical field, along with chemotaxis and injury stimulation, guides epithelial cell migration during wound healing. A laboratory study has shown enhanced movement of epithelial cells through application of electrical fields ($p=0.027$). Movement of epithelial cells does not occur in a linear fashion; rather the cells migrate approximately along the electrical field. Cells demonstrated the ability to change direction as much by as 180° in response to electrical fields. Interestingly, once cellular migration was observed, the authors of that study reversed the polarity of the electrical field and noticed a reversal of epithelial and fibroblast migration. Cells cultured without exposure to an electrical field exhibited a random orientation of the long axis of cell bodies or a cobblestone morphology. Epithelial cells cultured in the presence of an electrical field demonstrate an increase in the distance of cell movement ($p=0.046$). Under DC, endothelial cell orientation was seen as early as 4 hours after the onset of an electrical field. Longer electrical field stimulation, up to 3 days with 100 millivolts per millimeter (mV/mm), accelerated the orientation and elongation of endothelial cells compared to the control.

Angiogenesis is a critical component for processes in wound healing and is defined as the formation of new capillaries from pre-existing blood vessels. Insufficient angiogenesis can result in impaired wound healing and chronic wound formation. Electrical stimulation (ES) in its various forms enhances wound healing by promoting the migration of keratinocytes and macrophages, enhancing angiogenesis, stimulating fibroblasts, and influencing protein synthesis throughout the inflammatory, proliferative and remodeling phases of healing. Electrical signals stimulates angiogenesis and organize blood vessel formation. There is limited information on the influence of ES on angiogenesis after acute wounding in human skin, as most research is restricted to animal models. Animal studies show that angiogenesis is induced by ES in ischemic and non-ischemic rat limbs, and is facilitated by the increased expression of VEGF in muscle cells. Endogenous electric fields are able to direct the migration of epithelial cells during wound healing and may contribute to regulation of angiogenesis. Previous studies have shown that certain electrical currents, such as direct and alternating currents, are useful in treating diabetic foot ulcers, skin ulcers and chronic wounds.

Electrical stimulation is believed to restart or accelerate wound healing by imitating the natural electrical current that occurs in injured skin. PEMF stimulation decreases the doubling time of fibroblasts and endothelial cells in culture. PEMF increases p42/44 mitogen-activated protein (MAP) kinase activation, which is central to initiating cell responses and leads to cell proliferation. Electrical stimulation applied to injured tissue increases the migration of neutrophils and macrophages and stimulates fibroblasts. When skin is wounded, a change in electric potential occurs. This stimulus is the earliest guidance signal to initiate cell migration and re-epithelialization, and is essential to wound healing.

Figure 17:
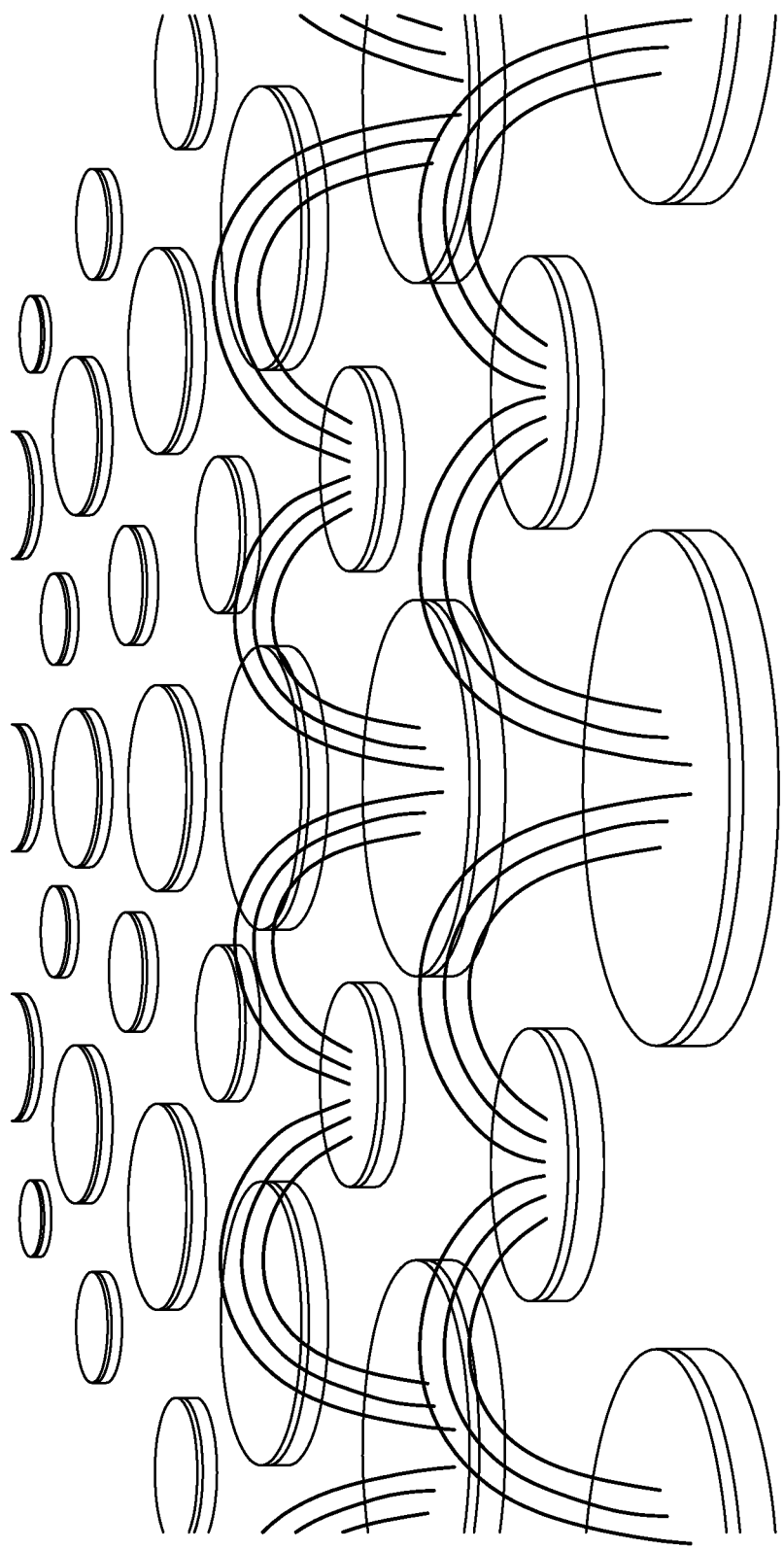
FIG. 17 is a schematic view showing representative field lines generated by juxtaposed metals, which metals may form at least a portion of each of a plurality of microneedles with electrical potential properties, according to at least one illustrated embodiment.

Microneedle Array with In Situ Anode and Cathode Structures (eBandage), Generates Electric Fields While Providing Antisepsis As best schematically illustrated in FIG. 17, eBandage microneedle batteries generate microcurrents in the presence of a conductive medium to direct the galvanic EMF (mV/mm) for enhanced wound healing. These microcurrents may, for example, be similar to or even replicate physiologic electric currents.

The microneedle array with in situ anode and cathode structures can have a number of advantageous in wound healing. For example, the microneedle array with in situ anode and cathode structures can generate physiologic levels of microcurrent (2-10 µA), that are known to be necessary for healing. The microneedle array with in situ anode and cathode structures can advantageously be flexible and/or portable with no need for external or power source separate and distinct from the microneedles themselves. The microneedle array with in situ anode and cathode structures can advantageously produce or deliver antibacterial metal ions.

Both copper and zinc ions are bactericidal. Bimetal nanostructures made from these metals may thus be excellent at killing both gram negative (*E. coli*) and gram positive (MRSA, Methicillin resistant *Staphylococcus aureus*) bacteria. The fields resulting from a Zn/Cu cell provide approximately (i.e., plus or minus 45%) 0.9V as mentioned above and are well above the 0.5V range of fields that affect stem cell behaviour, indicating that these fields could provide both accelerated wound healing through promoted cellular migration as well as antiseptic properties through the resultant metal ion production and contact with the metal element surfaces.

In addition to the antiseptic properties of the metal ions, and similar to the "eSkin" and HA (Hyaluronic acid) embodiments discussed above, one, more or all of the microneedles may comprise or may be loaded with antibacterial agents to reduce bacterial growth. Such can be used to limit or reduce bacterial growth on or in the bandage itself, for example during storage. Such can additionally or alternatively be delivered to a patient to limit or reduce bacterial growth in or proximate a wound being treated. These anti-bacterial agents may be distinct or different from the metal ions discussed above. For example, suitable anti-bacterial agents can include triclosan, triclocarban, and benzalkonium chloride.

The mechanism for delivery is not based on diffusion, as it is in other transdermal drug delivery products. Instead, the delivery mechanism is based on the temporary mechanical disruption of the skin and the placement of the drug or vaccine and/or anti-bacterial agent(s) within the epidermis, where to more readily reach the site of action. The drug or vaccine and/or anti-bacterial agent(s), in the form of biomolecules, can be encapsulated on or within the microneedles. The microneedles are then inserted into the skin, and transfer in a somewhat similar fashion as a drug like nitroglycerine is released into the bloodstream from a patch. The "cargo" (e.g., drug, vaccine, and/or anti-bacterial agent(s)) and/or needles dissolve within minutes, releasing the trapped cargo at the intended delivery site. The microneedles do not need to be removed and no dangerous or biohazardous substance is left behind on the skin, as the microneedles are made of a biodegradable substance. In microneedle devices, a small area (the size of a traditional transdermal patch) can be covered by tens to hundreds of microneedles formed in a matrix that penetrate (pierce) only the stratum corneum (e.g. the uppermost 50 µm of the skin), thus allowing the drug, vaccine, and/or anti-bacterial agent(s) to bypass this important barrier. The tiny microneedles are arranged in arrays to deliver sufficient amount of drug, vaccine, and/or anti-bacterial agent(s) to the patient for the desired therapeutic response.

Further, in at least any wound healing implementation, the microneedle structures are arranged to be juxta positioned around the wound when the eBandage microneedle battery array is applied to the skin. The bandage or substrate may be elastic, stretchable form an unstretched configuration to a stretched configuration under application of force by a user. Thus, the bandage can be applied to the substrate to the bodily interface tissue with the microneedles in contact with the bodily interface tissue by applying the substrate to the bodily interface tissue to surround a wound in the tissue in a stretched configuration, with respective ones of the microneedles juxtaposed from one another across the wound. On application, the bandage will tend to move towards the unstretched configuration under influence or biasing of the elastic property of the materials (e.g., substrate). Due to the flexible "pull-tight" link between two microneedle units, the wound is pulled together staunching bleeding and allowing for less scarring and more efficient wound healing. Here all other benefits of the microneedles structures could be combined The various embodiments described above can be combined to provide further embodiments. To the extent that they are not inconsistent with the specific teachings and definitions herein, all of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 62/197,421, filed Jul. 27, 2015 and U.S. Provisional Patent Application No. 62/288,305, filed Jan. 28, 2016, are incorporated herein by reference, in their entirety. Aspects of the embodiments can be modified, if necessary, to employ systems, circuits and concepts of the various patents, applications and publications to provide yet further embodiments.

We therefore claim:

1. A device, comprising:
    a plurality of microneedles, wherein the plurality of microneedles is composed of at least two discrete biocompatible substances, the at least two discrete biocompatible substances respectively comprise metals that have dissimilar electrical potentials from one another, the plurality of microneedles constituting a plurality of galvanic electrochemical half-cells of different electrochemical potentials, the galvanic electrochemical half-cells when exposed to water via insertion as at least one cathode and at least one anode within a skin tissue to complete an electrical circuit there between produce an electromotive force without any additional external chemical battery or power source.

2. The treatment device of claim 1 wherein the two discrete biocompatible substances includes a first electrical potential material that comprises copper compounds and a second electrical potential material that comprises zinc compounds, and the first electrical potential material forms the at least one cathode and the first electrical potential material forms the at least one anode.

3. The treatment device of claim 1 wherein the microneedles have principal dimensions of that are 750 microns or less.

4. The treatment device of claim 1 wherein the microneedles are composed of one or more of chitin, chitosan, carboxymethylcellulose, hydroxypropylcellulose, or polyvinylpyrrolidine, alone or in combination.

5. The treatment device of claim 1 wherein the microneedles are dissolvable in the bodily interface tissue.

6. The treatment device of claim 1 wherein the battery half-cells form electrochemical pairs that provide sufficient electromotive force to deliver an organoleptic effect.

7. The treatment device of claim 6, further comprising:
a cosmetic or pharmaceutical formulation.

8. The treatment device of claim 7 wherein the cosmetic or pharmaceutical formulation is coated on microneedles during manufacture of the treatment device and prior to delivery to an end user and prior to packaging of the treatment device in a sterile package.

9. The treatment device of claim 7 wherein the cosmetic or pharmaceutical formulation is shipped in a dispensable container with instructions, and is dispensed from the dispensable container on to the microneedles prior to application of the microneedles to the bodily interface tissue.

10. The treatment device of claim 7 wherein the cosmetic or pharmaceutical formulation is shipped in a dispensable container with instructions, and is dispensed from the dispensable container on to the bodily interface tissue prior to application of the microneedles to the bodily interface tissue.

11. The treatment device of claim 1 wherein at least one of the plurality of microneedles comprises a metal that releases metal ions on decomposition of the respective at least one of the plurality of microneedles, and the metal ions released on decomposition are bactericidal metal ions.

12. The device of claim 1, used for at least one of wound management or wrinkle reduction.

13. The device of claim 1 wherein the galvanic electrochemical half-cells formed by the plurality of microneedles are the sole power source for the device.

* * * * *